US012310394B2

(12) United States Patent
Mua et al.

(10) Patent No.: US 12,310,394 B2
(45) Date of Patent: May 27, 2025

(54) AEROSOL-GENERATING SUBSTRATE COMPRISING MICROCRYSTALLINE CELLULOSE

(71) Applicant: NICOVENTURES TRADING LIMITED, London (GB)

(72) Inventors: John Paul Mua, Advance, NC (US); Luis Monsalud, Kernersville, NC (US)

(73) Assignee: Nicoventures Trading Limited, London (GB)

( * ) Notice: Subject to any disclaimer, the term of this patent is extended or adjusted under 35 U.S.C. 154(b) by 356 days.

(21) Appl. No.: 17/876,604

(22) Filed: Jul. 29, 2022

(65) Prior Publication Data

US 2023/0051029 A1 Feb. 16, 2023

Related U.S. Application Data

(60) Provisional application No. 63/227,731, filed on Jul. 30, 2021.

(51) Int. Cl.

| | |
|---|---|
| ***A24B 15/16*** | (2020.01) |
| ***A24B 15/10*** | (2006.01) |
| ***A61M 15/06*** | (2006.01) |

(52) U.S. Cl.

CPC ............. *A24B 15/10* (2013.01); *A61M 15/06* (2013.01)

(58) Field of Classification Search

CPC ............. A24B 15/16; A24D 1/18; A24D 1/20

USPC ...... 15/10, 302, 16, 14, 243, 6; 1/20; 40/40, 40/46, 465, 50

See application file for complete search history.

(56) References Cited

U.S. PATENT DOCUMENTS

| | | | |
|---|---|---|---|
| 3,860,012 | A | 1/1975 | Selke |
| 3,894,544 | A | 7/1975 | Egri |
| 4,079,742 | A | 3/1978 | Rainer et al. |
| 4,646,764 | A | 3/1987 | Young et al. |
| 4,674,519 | A | 3/1987 | Keritsis et al. |
| 4,793,365 | A | 12/1988 | Sensabaugh et al. |
| 4,807,809 | A | 2/1989 | Pryor et al. |
| 4,848,374 | A | 7/1989 | Chard et al. |

(Continued)

FOREIGN PATENT DOCUMENTS

| | | |
|---|---|---|
| CN | 103005680 | 4/2013 |
| CN | 103263507 | 8/2013 |

(Continued)

OTHER PUBLICATIONS

"Modified Cross-Section Viscose Fibre: Galaxy VY—Trilobal Cellulosic Fibre," <htlps://web.archive.org/,veb/20160519070915/http://www.kelheim-fibres.com:80/pdf/TDS_Galaxy_VY_0814.pdf>, p. 1, 2014.

*Primary Examiner* — Eric Yaary

(74) *Attorney, Agent, or Firm* — Womble Bond Dickinson (US) LLP; Scott R. Breining

(57) ABSTRACT

The present disclosure provides a substrate which includes microcrystalline cellulose, a binder, an aerosol forming material, and optionally an active ingredient, a flavorant, or both an active ingredient and a flavorant. The final form of the substrate can be configured for use in aerosol generating components for aerosol delivery devices. Further provided are aerosol generating components and aerosol delivery devices including the substrate. Such devices utilize electrically generated heat or combustible ignition sources to heat the substrate, providing an inhalable substance in the form of an aerosol.

26 Claims, 7 Drawing Sheets

(56) References Cited

U.S. PATENT DOCUMENTS 4,924,887 A 5/1990 Raker et al.
4,947,874 A 8/1990 Brooks et al.
5,025,814 A 6/1991 Raker et al.
5,042,509 A 8/1991 Banerjee et al.
5,101,839 A 4/1992 Jakob et al.
5,105,831 A 4/1992 Banerjee et al.
5,105,836 A * 4/1992 Gentry ................. A24B 15/165 131/369
5,159,942 A 11/1992 Brinkley et al.
5,203,355 A 4/1993 Clearman et al.
5,369,723 A 11/1994 Counts et al.
5,396,911 A 3/1995 Casey, III et al.
5,417,229 A 5/1995 Summers et al.
5,501,237 A 3/1996 Young et al.
5,598,868 A 2/1997 Jakob et al.
5,666,977 A 9/1997 Higgins et al.
5,724,998 A 3/1998 Gellatly et al.
5,819,751 A 10/1998 Barnes et al.
6,138,683 A 10/2000 Hersh et al.
6,845,777 B2 1/2005 Pera
6,958,143 B2 10/2005 Choi et al.
7,032,601 B2 4/2006 Atchley et al.
7,056,541 B1 6/2006 Stahl et al.
7,428,905 B2 9/2008 Mua
7,507,427 B2 3/2009 Andersen et al.
7,647,932 B2 1/2010 Cantrell et al.
7,810,507 B2 10/2010 Dube et al.
7,833,555 B2 11/2010 Andersen et al.
7,861,728 B2 1/2011 Holton, Jr. et al.
7,900,637 B2 3/2011 Fagerstrom et al.
7,950,399 B2 5/2011 Winterson et al.
7,980,251 B2 7/2011 Winterson et al.
8,069,861 B2 12/2011 Sinclair
8,079,371 B2 12/2011 Robinson et al.
8,124,147 B2 2/2012 Cheng et al.
8,293,295 B2 10/2012 Andersen et al.
8,336,557 B2 12/2012 Kumar et al.
8,343,532 B2 1/2013 Dam et al.
8,402,976 B2 3/2013 Fernando et al.
8,424,541 B2 4/2013 Crawford et al.
8,469,036 B2 6/2013 Williams et al.
8,469,037 B2 6/2013 Liu et al.
8,528,569 B1 9/2013 Newton
8,529,875 B2 9/2013 Andersen
8,529,914 B2 9/2013 Fuisz et al.
8,545,870 B2 10/2013 Dupinay et al.
8,591,967 B2 11/2013 Andersen et al.
8,613,285 B2 12/2013 Fuisz
8,627,828 B2 1/2014 Strickland et al.
8,642,016 B2 2/2014 Chau et al.
8,714,163 B2 5/2014 Kumar et al.
8,741,348 B2 6/2014 Hansson et al.
8,747,562 B2 6/2014 Mishra et al.
8,828,361 B2 9/2014 Anderson
8,833,378 B2 9/2014 Axelsson et al.
8,846,075 B2 9/2014 Jonsson et al.
8,858,984 B2 10/2014 Dam et al.
8,863,755 B2 10/2014 Zhuang et al.
8,871,243 B2 10/2014 Fankhauser et al.
8,931,493 B2 1/2015 Sebastian et al.
8,945,593 B2 2/2015 LoCoco et al.
8,978,661 B2 3/2015 Atchley et al.
8,992,974 B2 3/2015 McCarty
9,027,567 B2 5/2015 Gee et al.
9,039,839 B2 5/2015 Beeson et al.
9,044,035 B2 6/2015 Jackson et al.
9,044,049 B2 6/2015 Winterson et al.
9,066,540 B2 6/2015 Atchley et al.
9,078,473 B2 7/2015 Worm et al.
9,084,439 B2 7/2015 Holton, Jr.
9,149,072 B2 10/2015 Conner et al.
9,155,321 B2 10/2015 Cantrell et al.
9,161,567 B2 10/2015 Shikata et al.
9,161,908 B2 10/2015 Nilsson
9,167,835 B2 10/2015 Sengupta et al.
9,185,931 B2 11/2015 Gao et al.
9,204,667 B2 12/2015 Cantrell et al.
9,237,768 B2 1/2016 Carroll et al.
9,307,787 B2 4/2016 Sun et al.
9,345,268 B2 5/2016 Stone et al.
9,358,296 B2 6/2016 McCarty
9,372,033 B2 6/2016 Lampe et al.
9,386,800 B2 7/2016 Sebastian et al.
9,402,414 B2 8/2016 Griscik et al.
9,402,809 B2 8/2016 Axelsson et al.
9,414,624 B2 8/2016 Carroll et al.
9,420,825 B2 8/2016 Beeson et al.
9,462,827 B2 10/2016 Carroll et al.
9,468,233 B2 10/2016 Macko et al.
9,474,303 B2 10/2016 Holton, Jr.
9,521,864 B2 12/2016 Gao et al.
9,565,867 B2 2/2017 Wittorff et al.
9,629,392 B2 4/2017 Holton, Jr.
9,635,881 B2 5/2017 Sjögren et al.
9,675,102 B2 6/2017 Hunt et al.
9,693,582 B2 7/2017 Carroll et al.
9,763,928 B2 9/2017 Duggins et al.
9,775,376 B2 10/2017 Cantrell et al.
9,788,571 B2 10/2017 Conner et al.
9,801,409 B1 10/2017 Smith
9,848,634 B2 12/2017 Fuisz
9,854,830 B2 1/2018 Gao et al.
9,854,831 B2 1/2018 Gao et al.
9,884,015 B2 2/2018 Gao et al.
9,907,748 B2 3/2018 Borschke et al.
9,925,145 B2 3/2018 Hübinette et al.
9,930,909 B2 4/2018 Gao et al.
9,974,334 B2 5/2018 Dooly et al.
9,986,756 B2 6/2018 Gao et al.
9,999,243 B2 6/2018 Gao et al.
10,039,309 B2 8/2018 Carroll et al.
10,045,976 B2 8/2018 Fusco et al.
10,092,715 B2 10/2018 Axelsson et al.
10,104,912 B2 10/2018 Sur
10,105,320 B2 10/2018 Gao et al.
10,130,120 B2 11/2018 Mishra et al.
10,143,230 B2 12/2018 Mishra et al.
10,149,850 B2 12/2018 Mishra et al.
10,172,810 B2 1/2019 McCarty
10,244,786 B2 4/2019 Gao et al.
10,292,431 B2 5/2019 White
10,315,889 B2 6/2019 Kreischer et al.
10,321,707 B2 6/2019 Klipfel et al.
10,327,473 B2 6/2019 Mironov
10,334,873 B2 7/2019 Mishra et al.
10,357,054 B2 7/2019 Marshall et al.
10,375,984 B2 8/2019 Hernandez Garcia et al.
10,390,557 B2 8/2019 Börjesson et al.
10,405,572 B2 9/2019 Batista
10,412,989 B2 9/2019 Klipfel et al.
10,420,365 B2 9/2019 Klipfel et al.
10,426,726 B2 10/2019 Neergaard
10,440,995 B2 10/2019 Sebastian et al.
10,463,070 B2 11/2019 Carroll et al.
10,532,046 B2 1/2020 Rogers et al.
10,543,205 B2 1/2020 Wittorff et al.
10,609,949 B2 4/2020 Hodin et al.
10,647,459 B2 5/2020 Persson
10,750,773 B2 8/2020 Yang et al.
10,791,756 B2 10/2020 Zuchuat et al.
10,798,969 B2 10/2020 Hejazi et al.
2004/0118422 A1 6/2004 Lundin et al.
2004/0129280 A1 7/2004 Woodson et al.
2004/0226568 A1 11/2004 Takeuchi et al.
2007/0031539 A1 2/2007 Calton
2008/0017203 A1 1/2008 Fagg et al.
2008/0081071 A1 4/2008 Sanghvi et al.
2008/0166395 A1 7/2008 Roush
2009/0023819 A1 1/2009 Axelsson
2009/0065013 A1 3/2009 Essen et al.
2009/0253754 A1 10/2009 Selmin et al.
2009/0301504 A1 12/2009 Worthen et al.
2010/0004294 A1 1/2010 Axelsson et al.
2010/0061940 A1 3/2010 Axelsson et al.

(56) References Cited

U.S. PATENT DOCUMENTS

2010/0187143 A1 7/2010 Essen et al.
2010/0260690 A1 10/2010 Kristensen et al.
2010/0294292 A1 11/2010 Hodin et al.
2011/0139164 A1 6/2011 Mua et al.
2011/0220130 A1 9/2011 Mua et al.
2011/0268809 A1 11/2011 Brinkley et al.
2012/0031415 A1 2/2012 Essen et al.
2012/0037175 A1 2/2012 Cantrell et al.
2013/0078307 A1 3/2013 Holton, Jr. et al.
2013/0118512 A1 5/2013 Jackson et al.
2013/0152953 A1 6/2013 Mua et al.
2013/0177646 A1 7/2013 Hugerth et al.
2013/0206150 A1 8/2013 Duggins et al.
2013/0251779 A1 9/2013 Svandal et al.
2013/0340773 A1 12/2013 Sebastian et al.
2014/0123986 A1 5/2014 Strickland et al.
2014/0130813 A1 5/2014 Strehle
2014/0154301 A1 6/2014 Chau et al.
2014/0255452 A1 9/2014 Reddick et al.
2014/0305448 A1 10/2014 Zuber et al.
2015/0068544 A1 3/2015 Moldoveanu et al.
2015/0068545 A1 3/2015 Moldoveanu et al.
2015/0071972 A1 3/2015 Holton, Jr. et al.
2015/0096573 A1 4/2015 Gao et al.
2015/0096574 A1 4/2015 Gao et al.
2015/0096576 A1 4/2015 Gao et al.
2015/0150302 A1 6/2015 Metrangolo et al.
2015/0157052 A1 6/2015 Ademe et al.
2015/0296868 A1 10/2015 Sutton
2015/0313283 A1 11/2015 Collett et al.
2016/0000140 A1 1/2016 Sebastian et al.
2016/0073676 A1 3/2016 Cantrell et al.
2016/0073689 A1 3/2016 Sebastian et al.
2016/0157515 A1 6/2016 Chapman et al.
2016/0192703 A1 7/2016 Sebastian et al.
2017/0007594 A1 1/2017 Borschke
2017/0055576 A1 3/2017 Beeson et al.
2017/0065000 A1 3/2017 Sears et al.
2017/0071250 A1 3/2017 Mironov et al.
2017/0164651 A1 6/2017 Mua et al.
2017/0165252 A1 6/2017 Mua et al.
2017/0172995 A1 6/2017 Repaka et al.
2017/0280764 A1 10/2017 Sahlén et al.
2017/0312261 A1 11/2017 Changoer et al.
2017/0318858 A1 11/2017 Hodin et al.
2018/0140007 A1 5/2018 Aspgren et al.
2018/0140521 A1 5/2018 Geonnotti et al.
2018/0140554 A1 5/2018 Wittorff
2018/0153211 A1 6/2018 Persson
2018/0235273 A1 8/2018 Carroll et al.
2018/0237273 A1 8/2018 Kreischer et al.
2018/0255826 A1 9/2018 Persson et al.
2018/0257801 A1 9/2018 Persson
2019/0037909 A1 2/2019 Greenbaum et al.
2019/0174812 A1 6/2019 Nielsen et al.
2019/0175581 A1 6/2019 Nielsen et al.
2019/0255035 A1 8/2019 Bruun
2019/0291900 A1 9/2019 Persson et al.
2020/0037638 A1 2/2020 Faraci et al.
2020/0093182 A1 3/2020 Monsalud et al.
2020/0128870 A1 4/2020 Hassler et al.
2020/0128880 A1 4/2020 Gage et al.
2020/0138706 A1 5/2020 Rudraraju et al.
2020/0154784 A1 5/2020 Sebastian et al.
2020/0154785 A1* 5/2020 Sebastian .............. A61M 15/06
2020/0253269 A1* 8/2020 Rousseau ............. A24B 15/302
2020/0275689 A1 9/2020 Lewerenz
2020/0281249 A1 9/2020 Sebastian et al.
2020/0297026 A1 9/2020 Kannisto et al.
2020/0305496 A1 10/2020 Gessesse
2020/0383372 A1 12/2020 Stahl et al.
2020/0383373 A1 12/2020 Stahl et al.
2021/0068447 A1 3/2021 Keller et al.
2021/0112848 A1 4/2021 Mua et al.
2021/0195938 A1 7/2021 Mua et al.

FOREIGN PATENT DOCUMENTS

CN 103494324 1/2014
CN 104856215 A 8/2015
CN 103750535 A 12/2015
CN 105192876 12/2015
CN 105595404 5/2016
CN 105747266 A 7/2016
CN 105919152 A 9/2016
CN 106235376 A 12/2016
CN 107616540 A 1/2018
CN 107616541 A 1/2018
CN 105768191 A 3/2018
CN 107927891 A 4/2018
CN 108143004 A 6/2018
CN 108208917 A 6/2018
CN 108323793 A 7/2018
CN 108451001 A 8/2018
CN 108451054 A 8/2018
CN 108497544 A 9/2018
CN 107259632 A 10/2018
CN 107307466 A 10/2018
CN 107319627 A 10/2018
CN 108652067 A 10/2018
CN 106368069 A 2/2019
EP 3616537 3/2020
EP 3756489 12/2020
GB 2534213 A 2/2018
WO WO 1997/032490 9/1997
WO WO 1997/032492 9/1997
WO WO 1999/063844 12/1999
WO WO 2010/113702 10/2010
WO WO 2011/101164 8/2011
WO WO 2012/133289 10/2012
WO WO 2013/178769 12/2013
WO WO 2015/055567 4/2015
WO WO 2015/082652 6/2015
WO WO 2015/176898 11/2015
WO WO 2015/177265 11/2015
WO WO 2016/050471 4/2016
WO WO 2016/156219 10/2016
WO WO 2016/156598 10/2016
WO WO 2016/162446 10/2016
WO WO 2017/041920 3/2017
WO WO 2017/051034 3/2017
WO WO 2017/068091 4/2017
WO WO 2017/068092 4/2017
WO WO 2017/068093 4/2017
WO WO 2017/068099 4/2017
WO WO 2017/077110 5/2017
WO WO 2017/077112 5/2017
WO WO 2017/108912 6/2017
WO WO 2018/033477 2/2018
WO WO 2018/162515 3/2018
WO WO 2018/172389 3/2018
WO WO 2018/122070 7/2018
WO WO 2018/152334 8/2018
WO WO 2018/197454 11/2018
WO WO 2018/215481 11/2018
WO WO 2019/036243 2/2019
WO WO 2019/105960 6/2019
WO WO 2019/115778 6/2019
WO WO 2019/162918 8/2019
WO WO 2020/013339 1/2020

* cited by examiner

AEROSOL-GENERATING SUBSTRATE COMPRISING MICROCRYSTALLINE CELLULOSE

CROSS-REFERENCE TO RELATED APPLICATIONS

This application claims priority to U.S. Provisional Application No. 63/227,731, filed on Jul. 30, 2021, and which is incorporated herein by reference in its entirety and for all purposes.

FIELD OF THE DISCLOSURE

The present disclosure relates to aerosol generating components, aerosol delivery devices, and aerosol delivery systems that utilize electrically-generated heat or combustible ignition sources to heat aerosol forming materials, generally without significant combustion, in order to provide an inhalable substance in the form of an aerosol for human consumption.

BACKGROUND

Many aerosol-generating articles have been proposed through the years as improvements upon, or alternatives to, smoking products based upon combusting tobacco for use. Some example alternatives have included devices wherein a solid or liquid fuel is combusted to transfer heat to tobacco or wherein a chemical reaction is used to provide such heat source. Additional example alternatives use electrical energy to heat tobacco and/or other aerosol generating substrate materials, such as described in U.S. Pat. No. 9,078,473 to Worm et al., which is incorporated herein by reference in its entirety.

The point of the improvements or alternatives to aerosol-generating articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., each of which are incorporated herein by reference in their entireties.

Articles that produce the taste and sensation of smoking by electrically heating tobacco, tobacco-derived materials, or other plant derived materials have suffered from inconsistent performance characteristics. For example, some articles have suffered from inconsistent release of flavors or other inhalable materials, inadequate loading of aerosol forming materials on substrates, or the presence of poor sensory characteristics. Accordingly, it can be desirable to provide a smoking article that can provide the sensations of cigarette, cigar, or pipe smoking, that does so without combusting the substrate material and that does so with advantageous performance characteristics.

Aerosol delivery devices wherein a solid fuel, such as carbon, is combusted to transfer heat to tobacco, as well as aerosol delivery devices utilizing electrically generated heat, have aerosol generating substrates as part of the aerosol generating component. In both types of devices, it would be advantageous to provide substrates with advantageous performance characteristics.

BRIEF SUMMARY

The present disclosure relates to a substrate for use in aerosol delivery devices that utilize electrically-generated heat or combustible ignition sources to heat the substrate in order to provide an inhalable substance in the form of an aerosol for human consumption. Accordingly, in one aspect, the disclosure provides a substrate for use in an aerosol delivery device, the substrate comprising: microcrystalline cellulose; one or more binders; and an aerosol forming material.

In some embodiments, the microcrystalline cellulose is present in an amount by weight of about 25% or more, based on the total dry weight of the substrate. In some embodiments, the microcrystalline cellulose is present in an amount by weight of 30% or more, based on the total dry weight of the substrate. In some embodiments, the microcrystalline cellulose is present in an amount by weight in a range from about 25 to about 60%, from about 30 to about 55%, or from about 35 to about 50%, based on the total dry weight of the substrate.

In some embodiments, the substrate further comprises wood pulp in an amount from about 5 to about 15% by weight, based on the total dry weight of the substrate.

In some embodiments, the binder is selected from the group consisting of cellulose ethers, alginates, starches, and combinations thereof. In some embodiments, the binder is a cellulose ether selected from the group consisting of methylcellulose, hydroxypropylcellulose, hydroxypropylmethylcellulose, hydroxyethyl cellulose, carboxymethylcellulose, and combinations thereof. In some embodiments, the binder is carboxymethylcellulose. In some embodiments, the binder is an alginate.

In some embodiments, the aerosol forming material is present in an amount by weight of about 10% or more, based on the total dry weight of the substrate. In some embodiments, the aerosol forming material is present in an amount by weight of about 20% or more, based on the total dry weight of the substrate. In some embodiments, the aerosol forming material is present in an amount by weight in a range from about 10 to about 70%. In some embodiments, the aerosol forming material is present in an amount by weight in a range from about 30 to about 60%.

In some embodiments, the aerosol forming material is selected from the group consisting of water, polyhydric alcohols, polysorbates, sorbitan esters, fatty acids, fatty acid esters, non-fatty acid esters, waxes, cannabinoids, terpenes, sugar alcohols, and combinations thereof. In some embodiments, the aerosol forming material is a polyhydric alcohol. In some embodiments, the polyhydric alcohol is selected from the group consisting of glycerol, propylene glycol, 1,3-propanediol, diethylene glycol, triethylene glycol, and combinations thereof.

In some embodiments, the substrate further comprises a flavorant, an active ingredient, or a combination thereof. In some embodiments, the active ingredient comprises a nicotine component.

In some embodiments, the substrate comprises: from about 30 to about 50% by weight of microcrystalline cellulose; from about 5 to about 10% by weight of wood pulp;

from about 5 to about 10% by weight of binder; and from about 30 to about 60% by weight of aerosol forming material.

In some embodiments, the binder is carboxymethylcellulose or sodium alginate

In some embodiments, the aerosol forming material is glycerol.

In some embodiments, the substrate is in the form of a sheet.

In some embodiments, the substrate is substantially free of tobacco material.

In some embodiments, the substrate is substantially free of nicotine.

In another aspect is provided an aerosol generating component for use with an aerosol delivery device, the aerosol generating component comprising a substrate comprising microcrystalline cellulose; one or more binders; and an aerosol forming material.

In some embodiments, the aerosol generating component further comprises an aerosol-generating material, wherein the aerosol-generating material comprises a tobacco material.

In some embodiments, the aerosol generating component further comprises a support, wherein the substrate is attached to the support.

In some embodiments, the support is planar.

In some embodiments, the substrate is blended with a tobacco material. In some embodiments, the tobacco material is present as a plurality of strips.

In some embodiments, the aerosol generating component comprises a plurality of strips of the substrate. In some embodiments, the aerosol generating component comprises multiple layers of the substrate.

In yet another aspect is provided an aerosol delivery device, comprising an aerosol generating component comprising a substrate comprising microcrystalline cellulose; one or more binders; and an aerosol forming material; a heat source configured to heat the aerosol generating component to form an aerosol; and an aerosol pathway extending from the aerosol generating component and extending along a length configured to convey the aerosol to a mouth portion of the aerosol delivery device.

In some embodiments, the heat source comprises either an electrically powered heating element or a combustible ignition source. In some embodiments, the heat source is a combustible ignition source comprising a carbon-based material. In some embodiments, the heat source is an electrically-powered heating element. In some embodiments, the heat source is a conductive heat source or an inductive heat source.

In some embodiments, the aerosol delivery device further comprises a power source electronically connected to the heating element. In some embodiments, the aerosol delivery device further comprises a controller configured to control power transmitted to the heating element by the power source.

The disclosure includes, without limitations, the following embodiments.

Embodiment 1: A substrate for use in an aerosol delivery device, the substrate comprising: microcrystalline cellulose; one or more binders; and an aerosol forming material.

Embodiment 2: The substrate of embodiment 1, wherein the microcrystalline cellulose is present in an amount by weight of about 25% or more, based on the total dry weight of the substrate.

Embodiment 3: The substrate of embodiment 1 or 2, wherein the microcrystalline cellulose is present in an amount by weight of 30% or more, based on the total dry weight of the substrate.

Embodiment 4: The substrate of embodiment 1, wherein the microcrystalline cellulose is present in an amount by weight in a range from about 25 to about 60%, from about 30 to about 55%, or from about 35 to about 50%, based on the total dry weight of the substrate.

Embodiment 5: The substrate of any one of embodiments 1-4, further comprising wood pulp in an amount from about 5 to about 15% by weight, based on the total dry weight of the substrate.

Embodiment 6: The substrate any one of embodiments 1-5, wherein the binder is selected from the group consisting of cellulose ethers, alginates, starches, and combinations thereof.

Embodiment 7: The substrate of any one of embodiments 1-6, wherein the binder is a cellulose ether selected from the group consisting of methylcellulose, hydroxypropylcellulose, hydroxypropylmethylcellulose, hydroxyethyl cellulose, carboxymethylcellulose, and combinations thereof.

Embodiment 8: The substrate of any one of embodiments 1-7, wherein the binder is carboxymethylcellulose.

Embodiment 9: The substrate of any one of embodiments 1-6, wherein the binder is an alginate.

Embodiment 10: The substrate of any one of embodiments 1-9, wherein the aerosol forming material is present in an amount by weight of about 10% or more, based on the total dry weight of the substrate.

Embodiment 11: The substrate of any one of embodiments 1-10, wherein the aerosol forming material is present in an amount by weight of about 20% or more, based on the total dry weight of the substrate.

Embodiment 12: The substrate of any one of embodiments 1-11, wherein the aerosol forming material is present in an amount by weight in a range from about 10 to about 70%.

Embodiment 13: The substrate of any one of embodiments 1-12, wherein the aerosol forming material is present in an amount by weight in a range from about 30 to about 60%.

Embodiment 14: The substrate of any one of embodiments 1-13, wherein the aerosol forming material is selected from the group consisting of water, polyhydric alcohols, polysorbates, sorbitan esters, fatty acids, fatty acid esters, non-fatty acid esters, waxes, cannabinoids, terpenes, sugar alcohols, and combinations thereof.

Embodiment 15: The substrate of any one of embodiments 1-14, wherein the aerosol forming material is a polyhydric alcohol.

Embodiment 16: The substrate of any one of embodiments 1-15, wherein the polyhydric alcohol is selected from the group consisting of glycerol, propylene glycol, 1,3-propanediol, diethylene glycol, triethylene glycol, and combinations thereof.

Embodiment 17: The substrate of any one of embodiments 1-16, further comprising a flavorant, an active ingredient, or a combination thereof.

Embodiment 18: The substrate of any one of embodiments 1-17, wherein the active ingredient comprises a nicotine component.

Embodiment 19: The substrate of any one of embodiments 1-18, comprising: from about 30 to about 50% by weight of microcrystalline cellulose; from about 5 to about 10% by weight of wood pulp; from about 5 to about 10% by weight of binder; and from about 30 to about 60% by weight of aerosol forming material.

Embodiment 20: The substrate of embodiment 19, wherein binder is carboxymethylcellulose or sodium alginate Embodiment 21: The substrate of embodiment 19 or 20, wherein the aerosol forming material is glycerol.

Embodiment 22: The substrate of any one of embodiments 1-21, in the form of a sheet.

Embodiment 23: The substrate of any one of embodiments 1-22, which is substantially free of tobacco material.

Embodiment 24: The substrate of any one of embodiments 1-23, which is substantially free of nicotine.

Embodiment 25: An aerosol generating component for use with an aerosol delivery device, the aerosol generating component comprising the substrate of any one of embodiments 1-25.

Embodiment 26: The aerosol generating component of embodiment 25, further comprising an aerosol-generating material, wherein the aerosol-generating material comprises a tobacco material.

Embodiment 27: The aerosol generating component of embodiment 25 or 26, further comprising a support, wherein the substrate is attached to the support.

Embodiment 28: The aerosol generating component of any one of embodiments 25-27, wherein the support is planar.

Embodiment 29: The aerosol generating component of any one of embodiments 25-28, wherein the substrate is blended with a tobacco material.

Embodiment 30: The aerosol generating component of any one of embodiments 26-29, wherein the tobacco material is present as a plurality of strips.

Embodiment 31: The aerosol generating component of any one of embodiments 25-30, comprising a plurality of strips of the substrate.

Embodiment 32: The aerosol generating component of any one of embodiments 25-30, comprising multiple layers of the substrate.

Embodiment 33: An aerosol delivery device, comprising: the aerosol generating component of any one of embodiments 25-32; a heat source configured to heat the aerosol generating component to form an aerosol; and an aerosol pathway extending from the aerosol generating component and extending along a length configured to convey the aerosol to a mouth portion of the aerosol delivery device.

Embodiment 34: The aerosol delivery device of embodiment 33, wherein the heat source comprises either an electrically powered heating element or a combustible ignition source.

Embodiment 35: The aerosol delivery device of embodiment 33 or 34, wherein the heat source is a combustible ignition source comprising a carbon-based material.

Embodiment 36: The aerosol delivery device of embodiment 33 or 34, wherein the heat source is an electrically-powered heating element.

Embodiment 37: The aerosol delivery device of embodiment 36, further comprising a power source electronically connected to the heating element.

Embodiment 38: The aerosol delivery device of embodiment 37, further comprising a controller configured to control power transmitted to the heating element by the power source Embodiment 39: The aerosol delivery device of any one of embodiments 33-38, wherein the heat source is a conductive heat source or an inductive heat source.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

Having thus described aspects of the disclosure in the foregoing general terms, reference will now be made to the accompanying drawings, which are not necessarily drawn to scale. The drawings are exemplary only, and should not be construed as limiting the disclosure.

Figure 1:
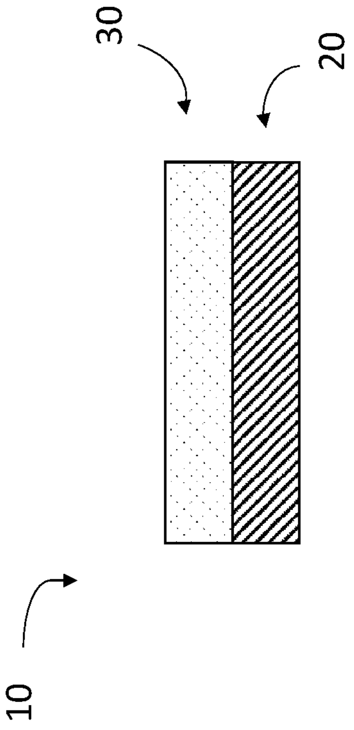
Figure 2:
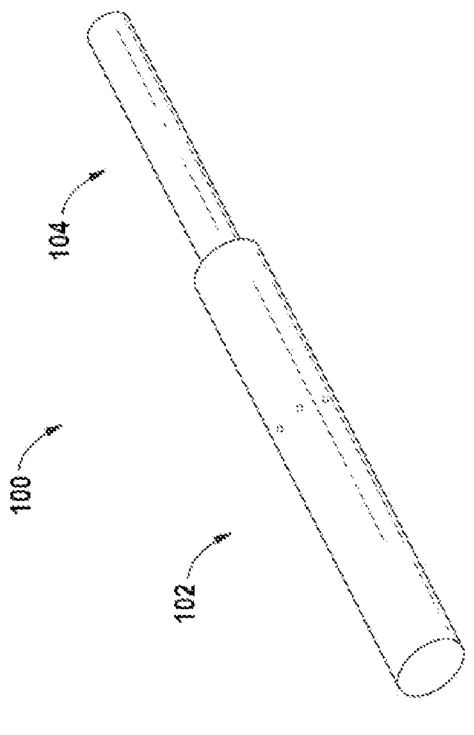
Figure 3:
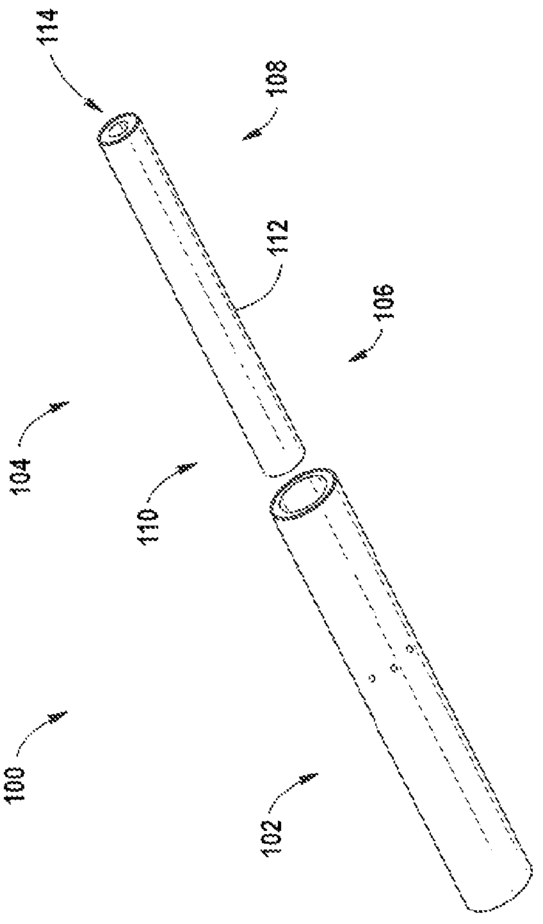
Figure 4:
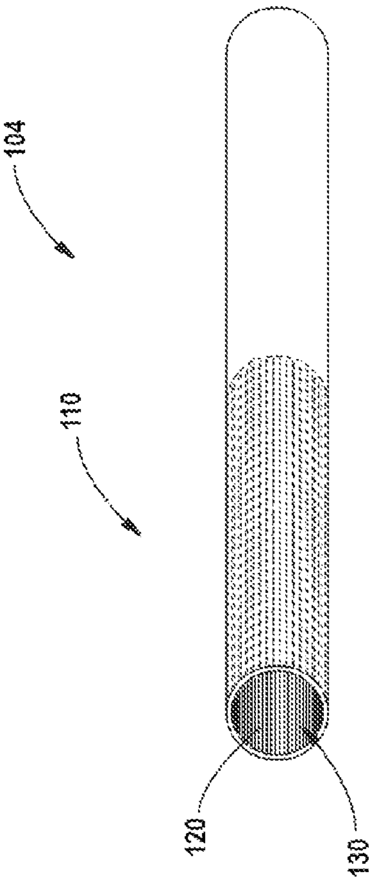
Figure 5:
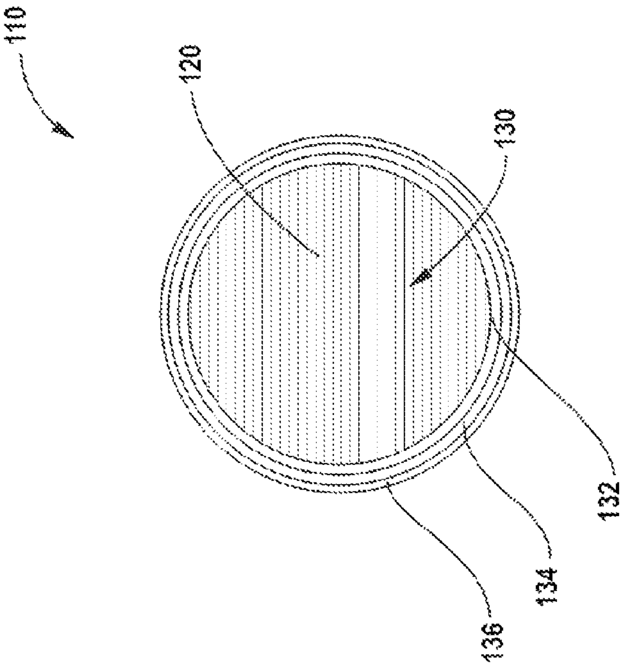
Figure 6:
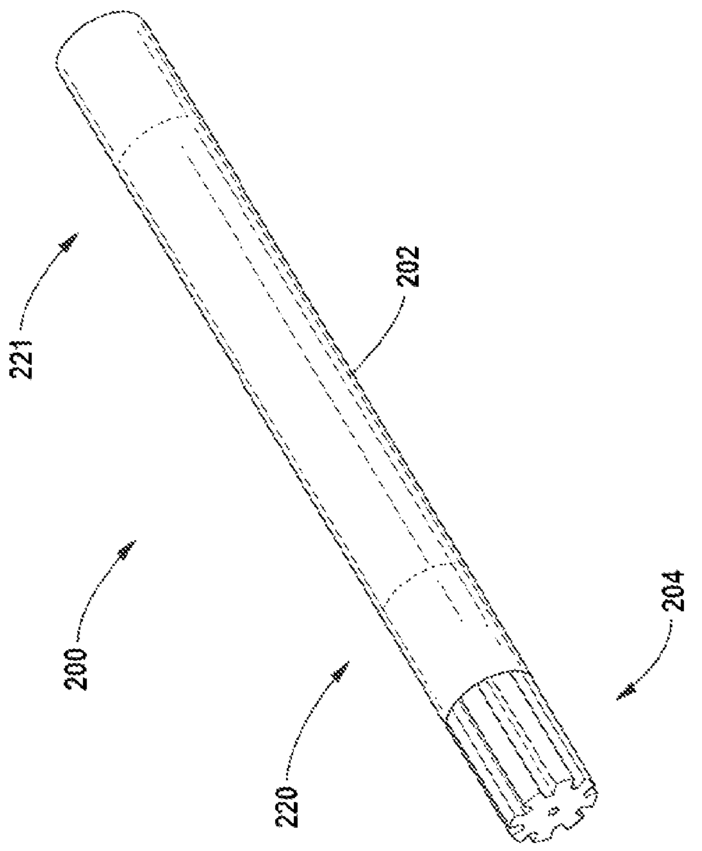
Figure 7:
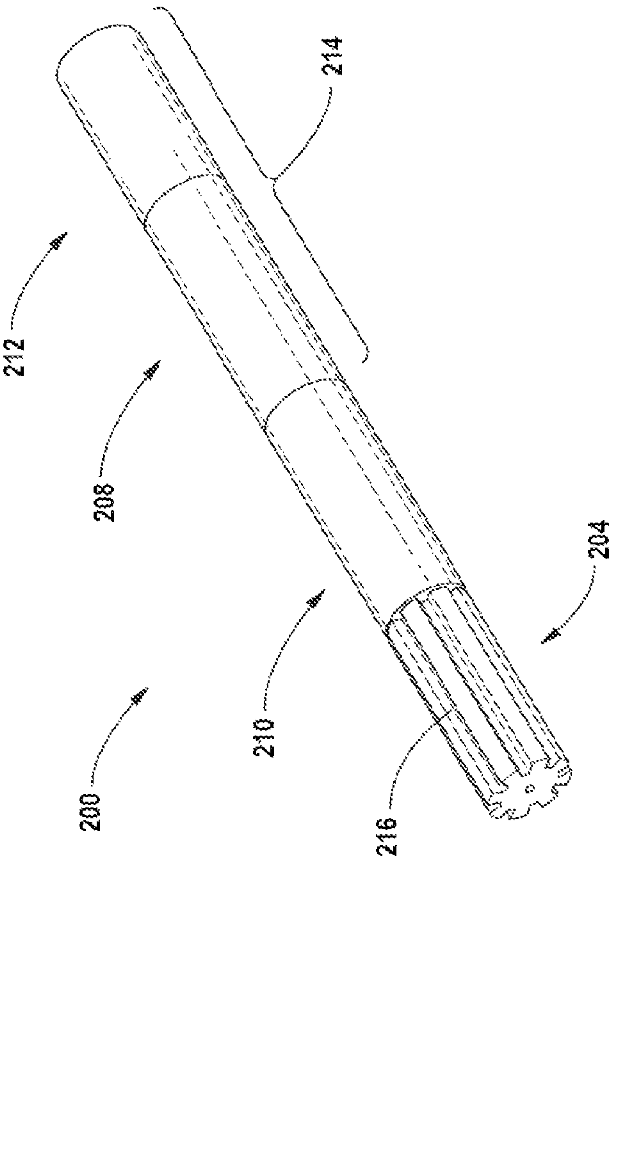

FIG. 1 illustrates a perspective schematic view of an aerosol generating component comprising a support and a substrate;

FIG. 2 illustrates a perspective view of an aerosol delivery device comprising a control body and an aerosol generating component, wherein the aerosol generating component and the control body are coupled to one another, according to an example embodiment of the present disclosure;

FIG. 3 illustrates a perspective view of the aerosol delivery device of FIG. 1 wherein the aerosol generating component and the control body are decoupled from one another, according to an example embodiment of the present disclosure;

FIG. 4 illustrates a perspective schematic view of an aerosol generating component, according to an example embodiment of the disclosure;

FIG. 5 illustrates a schematic cross-section drawing of a substrate portion of an aerosol generating component, according to an example embodiment of the present disclosure;

FIG. 6 illustrates a perspective view of an aerosol generating component, according to an example embodiment of the present disclosure; and FIG. 7 illustrates a perspective view of the aerosol generating component of FIG. 6 with an outer wrap removed, according to one embodiment of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements.

As used in this specification and the claims, the singular forms "a," "an," and "the" include plural referents unless the context clearly dictates otherwise.

The term "about" used throughout this specification is used to describe and account for small fluctuations. For example, the term "about" can refer to less than or equal to ±10%, such as less than or equal to ±5%, less than or equal to ±2%, less than or equal to ±1%, less than or equal to ±0.5%, less than or equal to ±0.2%, less than or equal to ±0.1% or less than or equal to ±0.05%. All numeric values herein are modified by the term "about," whether or not explicitly indicated. A value modified by the term "about" of course includes the specific value. For instance, "about 5.0" must include 5.0.

Reference to percent is intended to mean percent by weight unless otherwise indicated. All percentages by weight described herein are calculated on a dry weight basis, unless explicitly stated otherwise. Reference to "dry weight percent" or "dry weight basis" refers to weight on the basis of dry ingredients (i.e., all ingredients except water). A weight quoted on a dry weight basis refers to the whole of the slurry, material, or the like, other than the water or other solvent, and may include components which by themselves are liquid at room temperature and pressure, such as glycerol or other aerosol forming materials. Conversely, a weight percentage quoted on a wet weight basis refers to all components, including water or other solvent.

Substrate

As described hereinafter, example embodiments of the present disclosure relate to a substrate for use in an aerosol delivery device. The substrate may comprise a variety of materials, alone or in combinations. The substrate of the disclosure generally comprises a filler, a binder, an aerosol forming material, and optionally, an active ingredient, a flavorant, or both. Each of the substrate components is described further herein below Filler Substrates as disclosed herein comprise a filler. The filler may comprise materials such as non-tobacco botanical materials, cellulosic materials, wood fibers or pulp, starches, sugars, sugar alcohols, inorganic substances, inert materials, and the like, and combinations thereof. The amount of filler can vary. In some embodiments, the substrate comprises up to about 70% dry weight of filler, based on the total dry weight of the substrate. For example, in some embodiments, the substrate comprises from about 30% to about 70% of filler by weight, based on the total dry weight of the substrate. More than one filler may be used. In such embodiments, it is understood that reference to percent by weight of filler is intended to reflect the total amount of the combination of fillers present in the substrate.

Microcrystalline Cellulose

In some embodiments, microcrystalline cellulose ("mcc") is used as a filler in the substrate. In addition to functioning as a filler, the microcrystalline cellulose material used herein, in certain embodiments, can serve as a carrier, e.g., for flavorant. Microcrystalline cellulose has multiple uses, for example, as a texturizer, anti-caking agent, fat substitute, emulsifier, extender, and bulking agent, and as an excipient for direct compression, a binder, a disintegrant, an absorbent, a filler, a diluent, a lubricant, and an anti-adherent. In contrast to other cellulosic materials obtained directly from pulp, microcrystalline cellulose is a refined pulp product. Pulp is a lignocellulosic fibrous material prepared by chemically or mechanically separating cellulose fibers from wood, fiber crops, waste paper, or rags, while microcrystalline cellulose is distinguished as a purified, partially depolymerized cellulose.

Cellulose is a naturally occurring polymer comprised of glucose units connected by a 1-4 beta glycosidic bond. Linear chains of cellulose are bundled together as microfibril in the walls of plant cells. Each microfibril defines a crystalline structure that is insoluble in water and resistant to reagents. However, microfibrils include amorphous regions with weaker internal bonding. The crystalline structure is isolated to produce microcrystalline cellulose. Microcrystalline cellulose can only be produced from alpha cellulose (also known as "chemical cellulose"), which is a highly refined, insoluble, relatively higher molecular weight cellulose from which sugars, pectin, and other soluble materials have been removed. With respect to other types of cellulose, beta cellulose is defined as a more degraded form of cellulose, with less crystalline regions. Further, gamma cellulose is defined as short-chain hemicelluloses. Thus, beta cellulose and gamma cellulose are typically removed from an input employed to produce microcrystalline cellulose.

In the production of microcrystalline cellulose, alpha cellulose can initially be shredded and then immersed in a hot bath of mineral acid to dissolve the amorphous regions of the microfibrils while leaving the microcrystalline structures intact. The microcrystalline structures can then be subjected to hydrolysis to break down long polymer chains until the degree of polymerization decreases and levels off to a desired extent. Chemicals and impurities can then be removed through water-washing followed by drying. The resulting microcrystalline cellulose can be embodied as a fine white crystallized powder in raw form. Methods for forming microcrystalline cellulose from a plant material are set forth, for example, in U.S. Pat. No. 9,339,058 to Byrd, Jr. et al. and U.S. Pat. No. 10,774,472 to Sebastian, et al., both of which are incorporate herein by reference in their entirety. MCC materials are commercially available from suppliers such as DuPont de Nemours, Inc., Asahi Kasei Corporation, Sigachi Industries Limited, Accent Microcell Pvt. Ltd., and DFE Pharma GmbH & Co. KG. The microcrystalline cellulose may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof.

Microcrystalline cellulose is typically used in particulate form, and the size of the particles can vary. In certain embodiments, the microcrystalline cellulose material is in a very fine particulate form, such as particles having a D90 particle size of about 250 microns or less, such as about 170 microns or less, or about 150 microns or less. As used herein, the term "D90 particle size" means that 90% of the total particles are smaller than the given size. Particle size can be measured, for example, by laser diffraction or using a particle size analyzer.

In certain embodiments, the microcrystalline cellulose material has a relatively low bulk density, as compared to other types of cellulose materials, which is advantageous when a material with greater fill value is desired. Example ranges of bulk density for the microcrystalline cellulose material used in the present disclosure is about 0.50 g/mL or less, such as from about 0.26 to about 0.35 g/mL, or from about 0.26 to about 0.5 g/mL, as determined by measuring the volume of a known mass of powder.

In some embodiments, in comparison to other cellulosic materials, microcrystalline cellulose may advantageously provide one or more of improved texture, anti-caking, and anti-sticking properties to substrates comprising microcrystalline cellulose.

The quantity of microcrystalline cellulose present in the substrate may vary. In some embodiments, the substrate comprises, on a dry weight basis, about 25% or more by weight of microcrystalline cellulose, for example, from about 25 to about 60% by weight of microcrystalline cellulose, from about 30 to about 55%, or from about 35 to about 50% microcrystalline cellulose on a dry weight basis. In some embodiments, the substrate comprises from about 25, about 30, about 35, about 40, or about 45, to about 50%, about 55%, or about 60% by weight of microcrystalline cellulose on a dry weight basis.

Other Cellulosic Materials

In some embodiments, the filler comprises a further cellulosic material, such as a cellulosic material derived from flax, cotton linters, kenaf, hibiscus, hemp, tobacco, sisal, rice straw, or esparto. Other suitable cellulosic materials include, but are not limited to, cereal grains (e.g., maize, oat, barley, rye, buckwheat, and the like), sugar beet (e.g., FIBREX® brand filler available from International Fiber Corporation), bran fiber, and mixtures thereof.

In some embodiments, the cellulosic material is a cellulosic pulp or regenerated cellulose comprising at least about 90% cellulose by weight, such as about 90%, about 95%, about 99%, or even 100% cellulose. By "regenerated cellulose" is meant a natural cellulose that has been converted to a soluble or dissolving cellulosic derivative, and subsequently regenerated, typically by forming a fiber through polymer spinning, or through film polymer casting, precipitation or extrusion.

In some embodiments, the cellulosic material comprises a nanocellulose material. As used herein, "nanocellulose material" refers to cellulose materials having at least one average particle size dimension in the range of about 1 nm to about 100 nm. As a non-limiting example, a suitable nanocellulose material may be a fibrous material prepared from any suitable cellulose-containing material, such as grasses (e.g., bamboo), cotton, tobacco, algae, and other plant-based materials, wherein the fiber is further refined such that a nano-fibrillated cellulose fiber is produced.

Wood Fibers

In some embodiments, the filler comprises wood or wood-derived fibers (e.g., wood pulp). For example, in some embodiments, the substrate comprises, on a dry weight basis, from about 0 to about 15% of wood pulp, for example, from about 1% to about 15%, or from about 5 to about 15% of wood pulp. In some embodiments, the substrate comprises, on a dry weight basis, from about 5 to about 11%, or from about 5 to about 9% of wood pulp, for example, about 5, about 6, about 7, about 8, about 9, about 10, or about 11% of wood pulp. The presence of wood pulp can enhance the structural integrity of a substrate sheet material.

In other embodiments, the substrate is substantially or completely free of wood fibers or wood pulp. By "substantially free" of wood fibers or pulp is meant that no wood fibers or pulp have been intentionally added, beyond trace amounts that may be naturally present in e.g., a botanical or other plant material. For example, certain embodiments may be characterized as having less than 0.1% by dry weight, or less than 0.01% by dry weight, or less than 0.001% by dry weight, or 0% by dry weight of wood fibers or pulp, based on the total dry weight of the substrate.

In some embodiments, the filler comprises a combination of microcrystalline cellulose and wood pulp. In some embodiments, the filler is a combination of microcrystalline cellulose and wood pulp.

Non-Tobacco Botanicals

In some embodiments, the filler comprises a non-tobacco botanical material. As used herein, the term "botanical material" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, or other treatment processes capable of altering the chemical nature of the material). For the purposes of the present disclosure, a "botanical material" includes but is not limited to "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species). The botanical materials used in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods."

Non-limiting examples of non-tobacco botanical materials include without limitation acai berry (*Euterpe oleracea martius*), acerola (*Malpighia glabra*), alfalfa, allspice, *Angelica* root, anise (e.g., star anise), annatto seed, apple (*Malta domestica*), apricot oil, bacopa monniera, basil (*Ocimum basilicum*), bee balm, beet root, bergamot, blackberry (*Morus nigra*), black cohosh, black pepper, black tea, blueberries, boldo (*Peumus boldus*), borage, bugleweed, cacao, calamus root, camu (*Myrcaria dubia*), *cannabis*/hemp, caraway seed, catnip, catuaba, cayenne, cayenne pepper, chaga mushroom, chamomile, cherry, chervil, chocolate, cinnamon (*Cinnamomum cassia*), citron grass (*Cymbopogon citratus*), clary sage, cloves, coconut (*Cocos nucifera*), coffee, comfrey leaf and root, coriander seed, cranberry, dandelion, *Echinacea*, elderberry, elderflower, endro (*Anethum graveolens*), evening primrose, *eucalyptus*, fennel, feverfew, garlic, ginger (*Zingiber officinale*), gingko *biloba, ginseng*, goji berries, goldenseal, grape seed, grapefruit, grapefruit rosé (*Citrus paradisi*), graviola (*Annona muricata*), green tea, gutu kola, hawthorn, hibiscus flower (Hibiscus *sabdariffa*), honeybush, jiaogulan, kava, jambu (*Spilanthes oleraceae*), jasmine (*Jasminum officinale*), juniper berry (*Juniperus communis*), lavender, lemon (*Citrus limon*), licorice, lilac, Lion's mane, maca (*Lepidium meyenii*), marjoram, milk thistle, mints (menthe), oolong tea, orange (*Citrus sinensis*), oregano, *papaya*, pennyroyal, peppermint (*Mentha piperita*), potato peel, quince, red clover, rooibos (red or green), rosehip (*Rosa canina*), rosemary, sage, Saint John's Wort, *salvia* (*Salvia officinalis*), savory, saw palmetto, *silybum marianum*, slippery elm bark, sorghum bran hi-tannin, sorghum grain hi-tannin, spearmint (*Mentha spicata*), *spirulina*, sumac bran, thyme, turmeric, uva ursi, valerian, vanilla, wild yam root, wintergreen, withania somnifera, yacon root, yellow dock, yerba mate, and yerba santa.

In some embodiments, the substrate comprises a plant-derived non-tobacco material, including, but not limited to, eucalyptus, rooibos, star anise, fennel, hemp, flax, sisal, rice straw, esparto, and combinations thereof.

The quantity of non-tobacco botanical material present may vary, and is generally less than about 50% by weight of the substrate, based on the total dry weight of the substrate. For example, a non-tobacco botanical material may be present in a quantity of about 0%, about 0.1%, about 0.5%, about 1%, about 5%, about 10%, about 15%, about 20%, about 25%, about 30%, about 35%, about 40%, about 45%, or about 50% by weight of the substrate, based on the total dry weight of the substrate.

Starches and Sugars

In some embodiments, the filler comprises a starch, including native and modified starches. Certain starch materials may also be included in the substrate as a binder or other functional additive. "Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the beads based on the ability of the starch material to impart a specific organoleptic property to the beads. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Suitable starches include, but are not limited to, corn starch, rice starch, tapioca starch, and modified food starches. Certain starches are modified starches. A modified starch has undergone one or more structural modifications, often designed to alter its high heat properties. Some starches have been developed by genetic modifications, and are considered to be "modified" starches. Other starches are obtained and subsequently modified. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, enzyme treatment, acetylation, hydroxypropylation, and/or partial hydrolysis. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl di starch glycerol, and starch sodium octenyl succinate.

In some embodiments, the filler comprises corn starch, rice starch or rice flour, modified food starch, or a combination thereof. In other embodiments, the substrate is substantially or completely free of rice starch and rice flour. By "substantially free" of rice starch and rice flour is meant that no rice starch or flour has been intentionally added, beyond trace amounts that may be naturally present in e.g., another starch material. For example, certain embodiments may be characterized as having less than 0.1% by dry weight, or less than 0.01% by dry weight, or less than 0.001% by dry weight, or 0% by dry weight of rice starch and rice flour, based on the total dry weight of the substrate.

In some embodiments, the filler comprises a sugar. Suitable sugars include, but are not limited to, glucose, dextrose, fructose, maltose, and lactose.

In some embodiments, the filler comprises a sugar alcohol. Suitable sugar alcohols include, but are not limited to, sorbitol, mannitol, isomalt, maltitol, erythritol, and xylitol.

Inorganic and Inert Substances

In some embodiments, the filler comprises an inorganic substance or inert substance, such as, but not limited to, chitosan, carbons (graphite, diamond, fullerenes, graphene), quartz, granite, diatomaceous earth, calcium carbonate, calcium phosphate, clays, crustacean and other marine shells, or combinations thereof. In some embodiments, the substrate material may comprise inorganic fibers of various types (e.g., fiber glass, metal wires/screens, etc.) and/or (organic) synthetic polymers. In some embodiments, these "fibrous" materials may be unstructured (e.g., randomly distributed like the cellulose fibers in tobacco cast sheet) or structured (e.g., a wire mesh).

Binder

The substrate as disclosed herein comprises a binder. A binder (or a combination of binders) may be employed in an amount sufficient to provide the desired physical attributes and physical integrity to the substrate. The amount of binder utilized can vary. In some embodiments, the binder is present in an amount by weight from about 1%, 5%, 10%, 15%, 20%, 25%, 30% or 35% to about 40%, about 45%, about 50%, about 55%, or about 60% by weight, based on the dry weight of the substrate. Certain embodiments are characterized by a binder content of at least about 1% by weight, such as about 1 to about 30% by weight, or about 1 to about 20% by weight, or about 5 to about 15% by weight, based on the total wet weight of the substrate. In some embodiments, the binder is present in an amount by weight from about 5 to about 9%, or from about 7 to about 11%, or from about 6 to about 12%, based on the total dry weight of the substrate.

Typical binders can be organic or inorganic, or a combination thereof. Representative binders include povidone, alginate, seaweed hydrocolloids, pectin, starches, gums, carrageenan, pullulan, zein, cellulose derivatives, and the like, and combinations thereof. In some implementations, combinations or blends of two or more binder materials may be employed.

In some embodiments, the binder comprises an alginate, pectin, agar, agarose, gelatin, carrageenan, a gum, a cellulose derivative, pullulan, a starch or a derivative thereof, a silica or silicone compound, a clay, a polymer, or a combination thereof.

In some embodiments, the binder comprises an alginate, such as ammonium alginate, propylene glycol alginate, potassium alginate, or sodium alginate. Alginates, and particularly high viscosity alginates, may be employed in conjunction with controlled levels of free calcium ions as a crosslinking agent. In some embodiments, the substrate comprises, on a dry weight basis, from about 1 to about 15% of an alginate, for example, from about 5 to about 10% by weight of alginate, based on the total dry weight of the substrate.

In some embodiments, the binder comprises pectin. In some embodiments, the binder comprises alginate and/or pectin, which may be combined with a setting agent (such as a calcium source) during formation of the substrate. In some embodiments, the substrate may comprise a calcium-crosslinked alginate, a calcium- or acid-crosslinked pectin, or both.

In some embodiments, the binder comprises a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. In some embodiments, binder comprises xanthan gum, guar gum, gum Arabic, locust bean gum, gum tragacanth, or a combination thereof.

In some embodiments, the binder comprises a silica, fumed silica, sodium silicate, polydimethylsiloxane, kaolin, polyvinyl alcohol, or a combination thereof.

In some embodiments, the binder comprises a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose derivatives include methylcellulose, hydroxypropylcellulose ("HPC"), hydroxypropylmethylcellulose ("HPMC"), hydroxyethyl cellulose, and carboxymethylcellulose ("CMC"). Suitable cellulose ethers include hydroxypropylcellulose, such as Klucel H from Aqualon Co.; hydroxypropylmethylcellulose, such as Methocel K4MS from DuPont; hydroxyethylcellulose, such as Natrosol 250 MRCS from Aqualon Co.; methylcellulose, such as Methocel A4M, K4M, and E15 from DuPont.; and sodium carboxymethylcellulose, such as CMC 7HF, CMC 7LF, and CMC 7H4F from Aqualon Co. In some embodiments, the binder is one or more cellulose ethers (e.g., a single cellulose ether or a combination of several cellulose ethers, such as two or three, for example). In some embodiments, the binder is a cellulose ether selected from the group consisting of methylcellulose, hydroxypropylcellulose, hydroxypropylmethylcellulose, hydroxyethyl cellulose, carboxymethylcellulose, and combinations thereof. In some embodiments, the binder is carboxymethylcellulose. In some embodiments, the binder is hydroxypropylmethylcellulose.

In some embodiments, the substrate comprises carboxymethylcellulose in an amount by weight from about 5 to about 11%, or from about 7 to about 9%, based on the dry weight of the substrate.

Aerosol Forming Material

Substrates as disclosed herein comprise an aerosol forming material. Suitable aerosol forming materials include, but are not limited to, water, polyhydric alcohols, polysorbates, sorbitan esters, fatty acids, fatty acid esters, waxes, terpenes, sugar alcohols, tobacco extract, and combinations thereof. In some embodiments, the aerosol forming material may include water, polyhydric alcohols, polysorbates, sorbitan esters, fatty acids, fatty acid esters, triacetin, waxes, terpenes, cannabinoids, sugar alcohols, tobacco extract, or a combination of any thereof. Each of polyhydric alcohols, polysorbates, sorbitan esters, fatty acids, fatty acid esters, waxes, terpenes, and sugar alcohols are further described herein below.

The amount of aerosol forming material that is incorporated (e.g., loaded or impregnated) within the substrate may vary, and is generally such that the aerosol generating component comprising the substrate provides acceptable sensory and desirable performance characteristics. For example, it is highly preferred that sufficient amounts of aerosol forming material be employed in order to provide for the generation of a visible mainstream aerosol that in many regards resembles the appearance of tobacco smoke. The amount of forming materials within the aerosol generating component (e.g., the impregnated substrate) may be dependent upon factors such as the number of puffs desired per aerosol generating component.

In some embodiments, the substrate comprises the aerosol forming materials at a loading, on a dry weight basis, of at least about 0.1% by weight, at least about 0.5% by weight, at least about 1% by weight, at least about 5% by weight, at least about 10% by weight, at least about 15% by weight, at least about 20% by weight, at least about 25% by weight, at least about 30% by weight, at least about 35% by weight, at least about 40% by weight, at least about 45% by weight, at least about 50% by weight, at least about 55% by weight, at least about 60% by weight, at least about 65% by weight, at least about 70% by weight, at least about 75% by weight, or at least about 80% by weight, based on a total weight of the substrate. Example ranges of total aerosol forming materials include about 5 to about 80%, about 10 to about 70%, or about 20 to about 60%, such as about 15% to about 55%, about 15% to about 30%, or about 15% to about 25%, based on the total dry weight of the impregnated substrate. In some embodiments, the substrate comprises the aerosol forming materials in an amount by weight from about 10 to about 70%, about 40 to about 60%, about 30 to about 60%, or about 25 to about 45%, based on the dry weight of the substrate.

Polyhydric Alcohols

In some embodiments, the aerosol forming material comprises one or more polyhydric alcohols. Examples of polyhydric alcohols include glycerol (i.e., glycerin), propylene glycol, other glycols such as 1,3-propanediol, diethylene glycol, and triethylene glycol, and polyethylene glycols (e.g., PEG molecules with weight average molecular weight range of about 200 to about 2,000 Da).

In some embodiments, the polyhydric alcohol is selected from the group consisting of glycerol, propylene glycol, 1,3-propanediol, diethylene glycol, triethylene glycol, and combinations thereof. In some embodiments, the polyhydric alcohol is glycerol. In some embodiments, the aerosol forming material is glycerol.

In some embodiments, the polyhydric alcohol is a mixture of glycerol and propylene glycol. The glycerol and propylene glycol may be present in various ratios, with either component predominating depending on the intended application. In some embodiments, the glycerol and propylene glycol are present in a ratio by weight of from about 3:1 to about 1:3. In some embodiments, the glycerol and propylene glycol are present in a ratio by weight of about 3:1, about 2:1, about 1:1, about 1:2, or about 1:3. In some embodiments, the glycerol and propylene glycol are present in a ratio of about 1:1 by weight.

Polysorbates and Sorbitan Esters

In some embodiments, the aerosol forming material comprises one or more polysorbates. Examples of polysorbates include Polysorbate 60 (polyoxyethylene (20) sorbitan monostearate, Tween 60) and Polysorbate 80 (polyoxyethylene (20) sorbitan monooleate, Tween 80). The type of polysorbate used or the combination of polysorbates used depends on the intended effect desired, as the different polysorbates offer different attributes due to molecular sizes. For example, the polysorbate molecules increase in size from polysorbate 20 to polysorbate 80. Using smaller size polysorbate molecules creates less vapor quantity, but permits deeper lung penetration. This may be desirable when the user is in public where he would not want to create a large plume of "smoke" (i.e. vapors). Conversely, if a dense vapor is desired, which can convey the aromatic constituents of tobacco, larger polysorbate molecules can be employed. An additional benefit of using the polysorbate family of compounds is that the polysorbates lower the heat of vaporization of mixtures in which they are present.

In some embodiments, the aerosol forming material comprises one or more sorbitan esters. Examples of sorbitan esters include sorbitan monolaurate, sorbitan monostearate (Span 60), sorbitan monooleate (Span 20), and sorbitan tristearate (Span 65).

Fatty Acids, Esters, and Waxes

In some embodiments, the aerosol forming material comprises one or more fatty acids. Fatty acids may include short-chain, long-chain, saturated, unsaturated, straight chain, or branched chain carboxylic acids. Fatty acids generally include $C_4$ to $C_{28}$ aliphatic carboxylic acids. Non-limiting examples of short- or long-chain fatty acids include butyric, propionic, valeric, oleic, linoleic, stearic, myristic, and palmitic acids.

In some embodiments, the aerosol forming material comprises one or more fatty acid esters. Examples of fatty acid esters include alkyl esters, monoglycerides, diglycerides, and triglycerides. Examples of monoglycerides include monolaurin and glycerol monostearate. Examples of triglycerides include triolein, tripalmitin, tristearate, glycerol tributyrate, and glycerol trihexanoate.

In some embodiments, the aerosol forming material comprises one or more non-fatty acid esters. Examples of non-fatty acid esters include, but are not limited to, ethyl vanillate, ethyl laurate, diethyl suberate, triethyl citrate, triacetin, diacetin mixtures, benzyl benzoate, benzyl phenyl acetate, and propylene carbonate.

In some embodiments, the aerosol forming material comprises one or more waxes. Examples of waxes include carnauba, beeswax, candellila, which are known known to stabilize aerosol particles, improve palatability, or reduce throat irritation.

Terpenes

In some embodiments, the aerosol forming material comprises one or more terpenes. As used herein, the term "terpenes" refers to hydrocarbon compounds produced by plants biosynthetically from isopentenyl pyrophosphate. Non-limiting examples of terpenes include limonene, pinene, farnesene, myrcene, geraniol, fennel, and cembrene.

Sugar Alcohols

In some embodiments, the aerosol forming material comprises one or more sugar alcohols. Examples of sugar alcohols include sorbitol, erythritol, mannitol, maltitol, isomalt, and xylitol. Sugar alcohols may also serve as flavor enhancers to certain flavor compounds, e.g. menthol and other volatiles, and generally improve on mouthfeel, tactile sensation, throat impact, and other sensory properties, of the resulting aerosol.

In some embodiments, the aerosol forming material comprises glycerol, propylene glycol, diethylene glycol, triethylene glycol, tetraethylene glycol, 1,3-butylene glycol, erythritol, ethyl vanillate, ethyl laurate, a diethyl suberate, triethyl citrate, triacetin, a diacetin mixture, benzyl benzoate, benzyl phenyl acetate, tributyrin, lauryl acetate, lauric acid, myristic acid, propylene carbonate, or combinations of any thereof. In some embodiments, the aerosol forming material comprises, consists essentially of, or consists of glycerol.

Active Ingredient

In some embodiments, the substrate comprises one or more active ingredients. The active ingredient may be a component of the aerosol forming material, or may be impregnated or otherwise incorporated separately into the substrate. For example, the impregnation may be performed during preparation of the substrate material, after substrate formation, or both.

As used herein, an "active ingredient" refers to one or more substances belonging to any of the following categories: API (active pharmaceutical substances), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods". These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of synthetic organic compounds, proteins and peptides, polysaccharides and other sugars, lipids, inorganic compounds, and nucleic acid sequences, having therapeutic, prophylactic, or diagnostic activity. Non-limiting examples of active ingredients include those falling in the categories of botanical ingredients, stimulants, (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C, and/or cannabinoids, such as tetrahydrocannabinol (THC) and cannabidiol (CBD)), antioxidants, and nicotine components. The particular choice of active ingredients will vary depending upon the desired flavor, texture, and desired characteristics of the particular product.

The particular percentages of active ingredients present will vary depending upon the desired characteristics of the particular product. Typically, an active ingredient or combination thereof is present in a total concentration of at least about 0.001% by weight of the composition, such as in a range from about 0.001% to about 20%. In some embodiments, the active ingredient or combination of active ingredients is present in a concentration from about 0.1% w/w to about 10% by weight, such as, e.g., from about 0.5% w/w to about 10%, from about 1% to about 10%, from about 1% to about 5% by weight, based on the total weight of the composition. In some embodiments, the active ingredient or combination of active ingredients is present in a concentration of from about 0.001%, about 0.01%, about 0.1%, or about 1%, up to about 20% by weight, such as, e.g., from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the composition. Further suitable ranges for specific active ingredients are provided herein below.

Botanical

In some embodiments, the active ingredient comprises one or more non-tobacco botanicals. As used herein, the term "botanical ingredient" or "botanical" refers to any plant material or fungal-derived material, including plant material in its natural form (e.g., leaves, bark, fibers, stems, roots, seeds, flowers, fruits, pollen, husk, shells or the like) and plant material derived from natural plant materials, such as extracts or isolates from plant materials or treated plant materials (e.g., plant materials subjected to heat treatment, fermentation, or other treatment processes capable of altering the chemical nature of the material).

For the purposes of the present disclosure, a "botanical material" includes but is not limited to "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species). The botanical materials used in the present invention may comprise, without limitation, any of the compounds and sources set forth herein, including mixtures thereof. Certain botanical materials of this type are sometimes referred to as dietary supplements, nutraceuticals, "phytochemical s" or "functional foods."

Non-limiting examples of botanical materials, many of which are associated with antioxidant characteristics, include without limitation acai berry, alfalfa, allspice, aniseed, annatto seed, apricot oil, ashwagandha, bacopa monniera, baobab, basil, bay, bee balm, beet root, bergamot, black pepper, black tea, blueberries, borage seed oil, bugleweed, cacao, calamus root, cardamom, cassis, catnip, catuaba, cayenne pepper, *Centella asiatica*, chaga mushroom, Chai-hu, chamomile, cherry blossom, chervil, chive, chlorophyll, dark chocolate, cilantro, cinnamon, citrus, cloves, cocoa, coffee, comfrey leaf and root, black cohosh, *Cordyceps*, coriander, cranberry, cumin, curcumin, damiana, dandelion, *Dorstenia arifolia, Dorstenia odorata, echinacea*, elderflower, *eucalyptus*, fennel, feverfew, flax, *Galphimia glauca*, garlic, geranium, ginger, gingko *biloba, ginseng* (e.g., *Panax ginseng*), goji berries, goldenseal, grape seed, green tea, grapefruit, *Griffonia simplicifolia*, guarana, gutu kola, hawthorn, hazel, hemp, hibiscus flower, honeybush, hops, jasmine, jiaogulan, juniper, *Kaempferia parviflora* (*Thai ginseng*), kava, laurel, lavender, lemon, lemon balm, lemongrass, licorice, Lion's mane, lutein, maca, mace, marjoram, matcha, mulberry, *Nardostachys chinensis*, marjoram, milk thistle, mints (menthe), myrtle, nutmeg, olive, oolong tea, orange, oregano, *papaya*, paprika, pennyroyal, peppermint, pimento, potato peel, primrose, quercetin, red clover, resveratrol, *Rhizoma gastrodiae, Rhodiola*, rooibos, rooibos (red or green), rose essential oil, rosehip, rosemary, saffron, sage, clary sage, sandalwood, savory, saw palmetto, *Sceletium tortuosum*, Schisandra, *silybum marianum*, Skullcap, spearmint, Spikenard, *spirulina*, slippery elm bark, sorghum bran hi-tannin, sorghum grain hi-tannin, Saint John's Wort, star anise, sumac bran, tarragon, terpenes, thyme, tisanes, turmeric, *Turnera aphrodisiaca*, uva *ursi*, valerian, vanilla, *Viola odorata*, white mulberry, wild yam root, wintergreen, withania somnifera, yacon root, yellow dock, yerba mate, and yerba santa, In some embodiments, the active ingredient comprises or is derived from one or more botanicals or constituents, derivatives or extracts thereof, the botanical selected from *eucalyptus*, star anise, cocoa, and hemp.

When present, a botanical active ingredient is typically at a concentration of from about 0.01% w/w to about 10% by weight, such as, e.g., from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the composition.

Nicotine Component

In some embodiments, the active ingredient comprises a nicotine component. By "nicotine component" is meant any suitable form of nicotine (e.g., free base or salt) for providing systemic absorption of at least a portion of the nicotine present. The source of the nicotine may vary, and may be naturally derived or synthetic. Most preferably, the nicotine is naturally occurring and obtained as an extract from a *Nicotiana* species (e.g., tobacco). The nicotine can have the enantiomeric form S-(−)-nicotine, R-(+)-nicotine, or a mixture of S-(−)-nicotine and R-(+)-nicotine. Most preferably, the nicotine is in the form of S-(−)-nicotine (e.g., in a form that is virtually all S(−)-nicotine) or a racemic mixture composed primarily or predominantly of S-(−)-nicotine (e.g., a mixture composed of about 95 weight parts S-(−)-nicotine and about 5 weight parts R-(+)-nicotine). Most preferably, the nicotine is employed in virtually pure form or in an essentially pure form. Highly preferred nicotine that is employed has a purity of greater than about 95 percent, more preferably greater than about 98 percent, and most preferably greater than about 99 percent, on a weight basis.

Typically, the nicotine component is selected from the group consisting of nicotine free base and a nicotine salt. In some embodiments, nicotine is in its free base form. Nicotine may be tobacco-derived (e.g., a tobacco extract) or non-tobacco derived (e.g., synthetic or otherwise obtained). In various embodiments, the impregnated substrate may comprise a nicotine component. In various embodiments, the impregnated substrate may not comprise a nicotine component. In some embodiments, the impregnated substrate may comprise a non-tobacco-derived nicotine component.

Typically, the nicotine component (calculated as the free base) when present, is in a concentration of at least about 0.001% by weight of the impregnated substrate, such as in a range from about 0.001% to about 10%. In some embodiments, the nicotine component is present in a concentration from about 0.1% w/w to about 10% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the impregnated substrate. In some embodiments, the nicotine component is present in a concentration from about 0.1% w/w to about 3% by weight, such as, e.g., from about 0.1% w/w to about 2.5%, from about 0.1% to about 2.0%, from about 0.1% to about 1.5%, or from about 0.1% to about 1% by weight, calculated as the free base and based on the total weight of the impregnated substrate. These ranges can also apply to other active ingredients noted herein.

In some embodiments, the substrate of the disclosure can be characterized as completely free or substantially free of nicotine components. By "substantially free of nicotine components" is meant that no nicotine has been intentionally added, beyond trace amounts that may be naturally present in e.g., a botanical material. For example, certain embodiments can be characterized as having less than 0.001% by weight of nicotine, or less than 0.0001%, or even 0% by weight of nicotine, calculated as the free base.

Cannabinoids

In some embodiments, the active ingredient comprises one or more cannabinoids. As used herein, the term "cannabinoid" refers to a class of diverse natural or synthetic chemical compounds that acts on cannabinoid receptors (e.g., CB1 and CB2) in cells that alter neurotransmitter release in the brain. Cannabinoids are cyclic molecules exhibiting particular properties such as the ability to easily cross the blood-brain barrier. Cannabinoids may be naturally occurring (phytocannabinoids) from plants such as *canna-*

*bis*, (endocannabinoids) from animals, or artificially manufactured (synthetic cannabinoids). *Cannabis* species express at least 85 different phytocannabinoids, and these may be divided into subclasses, including cannabigerols, cannabichromenes, cannabidiols, tetrahydrocannabinols, cannabinols and cannabinodiols, and other cannabinoids, such as cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), and tetrahydrocannabivarinic acid (THCV A).

In some embodiments, the cannabinoid is selected from the group consisting of cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), tetrahydrocannabivarinic acid (THCV A), and mixtures thereof. In some embodiments, the cannabinoid comprises at least tetrahydrocannabinol (THC). In some embodiments, the cannabinoid is tetrahydrocannabinol (THC). In some embodiments, the cannabinoid comprises at least cannabidiol (CBD). In some embodiments, the cannabinoid is cannabidiol (CBD). In some embodiments, the CBD is synthetic CBD. Notably, CBD has a log P value of about 6.5, making it insoluble in an aqueous environment (e.g., saliva).

In some embodiments, the cannabinoid (e.g., CBD) is added to the substrate in the form of an isolate. An isolate is an extract from a plant, such as *cannabis*, where the active material of interest (in this case the cannabinoid, such as CBD) is present in a high degree of purity, for example greater than 95%, greater than 96%, greater than 97%, greater than 98%, or around 99% purity.

In some embodiments, the cannabinoid is an isolate of CBD in a high degree of purity, and the amount of any other cannabinoid in the substrate is no greater than about 1% by weight of the substrate, such as no greater than about 0.5% by weight of the substrate, such as no greater than about 0.1% by weight of the substrate such as no greater than about 0.01% by weight of the substrate.

The choice of cannabinoid and the particular percentages thereof which may be present within the disclosed substrate will vary depending upon the desired characteristics of the substrate.

In some embodiments, the cannabinoid (such as CBD) is present in the substrate in a concentration of at least about 0.001% by weight of the substrate, such as in a range from about 0.001% to about 2% by weight of the substrate. In some embodiments, the cannabinoid (such as CBD) is present in the substrate in a concentration of from about 0.1% to about 1.5% by weight, based on the total weight of the substrate. In some embodiments, the cannabinoid (such as CBD) is present in a concentration from about 0.4% to about 1.5% by weight, based on the total weight of the substrate.

Alternatively, or in addition to the cannabinoid, the active ingredient may include a cannabimimetic, which is a class of compounds derived from plants other than *cannabis* that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids. Such compounds can be used in the same amounts and ratios noted herein for cannabinoids.

In some embodiments, the active ingredient comprises nicotine and cannabidiol (CBD). In some embodiments, the active ingredient comprises nicotine, cannabidiol (CBD), and THC (tetrahydrocannabinol). In some embodiments, the active ingredient comprises nicotine, caffeine, taurine, theine, vitamins such as B6 or B12 or C, melatonin, cannabinoids, or constituents, derivatives, or combinations thereof.

Terpenes

Active ingredients suitable for use in the present disclosure can also be classified as terpenes, many of which are associated with biological effects, such as calming effects. Terpenes are understood to have the general formula of $(C_5H_8)_n$ and include monoterpenes, sesquiterpenes, and diterpenes. Terpenes can be acyclic, monocyclic or bicyclic in structure. Some terpenes provide an entourage effect when used in combination with cannabinoids or cannabimimetics. Examples include beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, and germacrene, which may be used singly or in combination.

In some embodiments, the terpene is a terpene derivable from a phytocannabinoid producing plant, such as a plant from the stain of the *Cannabis sativa* species, such as hemp. Suitable terpenes in this regard include so-called "C10" terpenes, which are those terpenes comprising 10 carbon atoms, and so-called "C15" terpenes, which are those terpenes comprising 15 carbon atoms. In some embodiments, the active ingredient comprises more than one terpene. For example, the active ingredient may comprise one, two, three, four, five, six, seven, eight, nine, ten or more terpenes as defined herein. In some embodiments, the terpene is selected from pinene (alpha and beta), geraniol, linalool, limonene, carvone, eucalyptol, menthone, iso-menthone, piperitone, myrcene, beta-bourbonene, germacrene and mixtures thereof.

Terpenes and/or cannabinoids may be present in the substrate as an active ingredient, as an aerosol forming material, or as a flavoring component. The amount of terpenes and/or cannabinoids present may vary accordingly based on their intended purpose.

Flavorant

In some embodiments, the substrate comprises a flavorant. The flavorant may be a component of the aerosol forming material, or may be impregnated separately. The impregnation may be performed during preparation of the substrate material, after substrate formation, or both. As used herein, reference to a "flavorant" refers to compounds or components that can be aerosolized and delivered to a user and which impart a sensory experience in terms of taste and/or aroma. Flavorants may be natural or synthetic, and the character of the flavors imparted thereby may be described, without limitation, as fresh, sweet, herbal, confectionary, floral, fruity, or spicy. Some examples of flavorants include, but are not limited to, aloe vera, aniseed, apple, Asian spices, bacopa monniera, basil, bay leaves, beefsteak plant, bergamot, berry, *betel*, blueberry, bourbon, camphene, *cannabis*, caraway, cardamom, *carvi*, cascarilla, *cassia*, cassis, celery, chamomile, cherry, cherry blossom, chive, cilantro, cinnamon, citrus fruits, clementine, clove, cocoa, coffee, cognac, coriander, cranberry, cucumber, cumin, *curcuma*, damien, dragon fruit, Drambuie, durian, elderflower, *eucalyptus*, eugenol, fennel, fenugreek, flax, geranium, gin, ginger, *Ginkgo biloba*, grape, guayusa, hazel, hemp, hibiscus, honeybush, honey essence, *hydrangea*, Indian spices, jasmine, juniper, khat, lavender, laurel, lemon, lemongrass, lemon balm, lemon oil, lemon peel, licorice, lime, limonene, mace, Japanese white bark *magnolia* leaf, mango, maple, marjoram, matcha, mate, menthol, mint, myrtle, mulberry, naswar, nutmeg, olive, orange blossom, orange oil, orange skin, oregano, *papaya*, paprika, peach, peppermint, piment, pimento, pine, rhubarb, rooibos, rosemary, rose hip, rose oil, rum, saffron, sage, sandalwood, scotch, shisha, spearmint, strawberry, tarragon, tea such as green tea or black tea, tequila, terpenes, thyme, tobacco, tropical fruit, turmeric, valerian, vanilla, *verbena*, wasabi, whiskey, wintergreen, withania somnifera, yerba mate, yerba santa, ylang-ylang, and combinations thereof.

Flavorants may further include flavor enhancers, bitterness receptor site blockers, sensorial receptor site activators or stimulators, and trigeminal sensates, As used herein, "trigeminal sensate" refers to a flavoring agent which has an effect on the trigeminal nerve, producing sensations including heating, cooling, tingling, and the like. Non-limiting examples of trigeminal sensate flavoring agents include capsaicin, citric acid, menthol, Sichuan buttons, erythritol, and cubebol.

Further non-limiting examples include flavorings and flavor packages of the type and character traditionally used for the flavoring of cigarette, cigar, and pipe tobaccos. See also, Leffingwell et al., Tobacco Flavoring for Smoking Products, R. J. Reynolds Tobacco Company (1972), which is incorporated herein by reference. Flavoring agents may comprise components such as terpenes, terpenoids, aldehydes, ketones, esters, and the like. Syrups, such as high fructose corn syrup, also can be employed. Some examples of plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components is variable based upon factors such as the sensory characteristics that are desired for the smoking article, their affinity for the substrate material, their solubility, and other physiochemical properties. The present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants. Additional flavorants, flavoring agents, additives, and other possible enhancing constituents are described in U.S. patent application Ser. No. 15/707,461 to Phillips et al., which is incorporated herein by reference in its entirety.

The quantity of flavorant present may vary, and when present, is generally less than about 30%, or less than about 20% by weight of the impregnated substrate. For example, a flavorant may be present in a quantity of from about 0.1%, about 0.5%, about 1%, or about 5%, to about 10%, about 20%, or about 30% by weight of the impregnated substrate.

Water

The moisture (e.g., water) content of the substrate may vary. For example, in some embodiments, the substrate comprises from about 0% to about 30% water. In some embodiments, the substrate is dried to remove at least a portion of the water present during preparation. In some embodiments, after drying, the substrate comprises from about from about 3 to about 21% water, based on the total weight of the substrate. In some embodiments, after drying, the substrate comprises from about 8 to about 10, or from about 12 to about 18% water, based on the total weight of the substrate. In some embodiments, after drying, the substrate comprises from about 15 to about 21% water, based on the total weight of the substrate.

Colorant

In some embodiments, the substrate comprises a colorant. The addition of a colorant may alter the visual appearance of the substrate. The presence of colorant may enhance the visual appearance of the substrate and/or an aerosol generating component comprising the substrate. By adding a colorant to the substrate, the substrate may be color-matched to other components of the aerosol generating component or to other components of an article comprising the substrate.

A variety of colorants may be used depending on the desired color of the substrate. The color of the substrate may be, for example, white, green, red, purple, blue, brown or black. Other colors are also contemplated herein. Natural or synthetic colorants, such as natural or synthetic dyes, food-grade colorants and pharmaceutical-grade colorants may be used. In certain embodiments, the colorant is caramel, which may confer the substrate with a brown appearance. In such embodiments, the color of the substrate may be similar to the color of other components (such as tobacco material) in an aerosol generating component comprising the substrate. In some embodiments, the addition of a colorant to the substrate renders it visually indistinguishable from other components. The colorant may be incorporated during the formation of the substrate (e.g. when forming a slurry comprising the materials that form the substrate) or it may be applied to the substrate after its formation (e.g. by spraying it onto the substrate).

Tobacco Material

In some embodiments, the substrate, or the aerosol generating component comprising the substrate, or both, comprise a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. Hersperis, *N. pauciflora, N. petunioides, N. quadrivalvis, N. repanda, N. rotundifolia, N. solanifolia*, and *N. spegazzinii*. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No.

7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within a substrate as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The substrate disclosed herein can include processed tobacco parts or pieces, cured and aged tobacco in essentially natural lamina and/or stem form. In certain embodiments, the tobacco material comprises solid tobacco material selected from the group consisting of lamina and stems. The tobacco that is used for the substrate most preferably includes tobacco lamina, or a tobacco lamina and stem mixture (of which at least a portion is smoke-treated). Portions of the tobacco may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the substrate may incorporate tobacco that has been fermented. See, also, the types of tobacco processing techniques set forth in PCT WO2005/063060 to Atchley et al., which is incorporated herein by reference.

The tobacco material is typically used in a form that can be described as particulate, for example, shredded, ground, granulated, pulp, or powder form. In some embodiments, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco material is provided in a finely divided or powder type of form may vary. Preferably, plant parts or pieces are milled, comminuted, ground or pulverized into a particulate form using equipment and techniques for grinding, milling, or the like. The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground, pulped or milled pieces of plants or portions thereof can have moisture contents of less than about 25 weight percent, often less than about 20 weight percent, and frequently less than about 15 weight percent. Most preferably, the plant material is relatively dry in form during grinding or milling, using equipment such as hammer mills, cutter heads, air control mills, or the like. For example, tobacco parts or pieces may be ground or milled when the moisture content thereof is less than about 15 weight percent or less than about 5 weight percent.

For the preparation of substrates, it is typical for a harvested plant of the *Nicotiana* species to be subjected to a curing process. The tobacco materials incorporated within the substrates as disclosed herein are generally those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.,* 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.,* 21, 305-320 (2005) and Staaf et al., *Beitrage Tabakforsch. Int.,* 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco on a dry weight basis.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

In some embodiments, the type of tobacco material is selected such that it is initially visually lighter in color than other tobacco materials to some degree (e.g., whitened or bleached). Tobacco pulp can be whitened in certain embodiments according to any means known in the art. For example, bleached tobacco material produced by various whitening methods using various bleaching or oxidizing agents and oxidation catalysts can be used. Example oxidizing agents include peroxides (e.g., hydrogen peroxide), chlorite salts, chlorate salts, perchlorate salts, hypochlorite salts, ozone, ammonia, potassium permanganate, and combinations thereof. Example oxidation catalysts are titanium dioxide, manganese dioxide, and combinations thereof. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; U.S. Pat. Nos. 9,420,825 and 10,772,349 to Beeson et al.; and U.S. Pat. No. 9,950,858 to Byrd Jr. et al.; as well as in US Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas; WO2020128971 and WO2021048769 to McClanahan et al; WO2013122948A1 to Beeson et al.; WO2018/083114 to Bjorkholm; and WO2021048768 and WO2021048770A1 to Zawadzki et al., all of which are incorporated herein by reference.

In some embodiments, the whitened tobacco material can have an ISO brightness of at least about 50%, at least about 60%, at least about 65%, at least about 70%, at least about 75%, or at least about 80%. In some embodiments, the whitened tobacco material can have an ISO brightness in the range of about 50% to about 90%, about 55% to about 75%, or about 60% to about 70%. ISO brightness can be measured according to ISO 3688:1999 or ISO 2470-1:2016.

In some embodiments, the whitened tobacco material can be characterized as lightened in color (e.g., "whitened") in comparison to an untreated tobacco material. White colors are often defined with reference to the International Commission on Illumination's (CIE's) chromaticity diagram. The whitened tobacco material can, in certain embodiments, be characterized as closer on the chromaticity diagram to pure white than an untreated tobacco material.

The tobacco material may be processed to remove at least a portion of the nicotine present. Suitable methods of extracting nicotine from tobacco material are known in the art. In some embodiments, the tobacco material is substantially free of nicotine. By "substantially free" is meant that only trace amounts are present in the tobacco material. For example, in certain embodiments, the tobacco material can be characterized as having less than 0.001% by weight of nicotine, or less than 0.0001%, or even 0% by weight of nicotine, calculated as the free base, and based on the total weight of the tobacco material.

The quantity of tobacco material present may vary, and is generally less than about 65% by weight of the substrate, based on the total weight of the substrate. For example, a tobacco material may be present in a quantity from about 0%, about 0.1%, about 0.5%, about 1%, about 5%, about 10%, about 15%, about 20%, about 25%, about 30%, or about 35%, to about 40%, about 45%, about 50%, about 55%, about 60%, or about 65% by weight of the substrate, based on the total dry weight of the substrate.

In some embodiments, the substrate of the disclosure can be characterized as completely free or substantially free of any tobacco material (e.g., any embodiment as disclosed herein may be completely or substantially free of any tobacco material). By "substantially free" is meant that no tobacco material has been intentionally added, beyond trace amounts that may be naturally present in e.g., botanical or herbal material. For example, certain embodiments can be characterized as having less than 0.5% by weight tobacco material, less than 0.1% by weight tobacco material, less than 0.01% by weight tobacco material, or less than 0.001%, or even 0% by weight tobacco material, based on the total wet weight of the substrate.

Tobacco-Derived Materials

In some embodiments, the substrate further comprises a tobacco extract, such as an aqueous tobacco extract, added either as a component of the aerosol forming material, or added separately (e.g., during substrate preparation, or impregnated in the substrate after formation). "Tobacco extract" as used herein refers to the isolated components of a tobacco material that are extracted from solid tobacco pulp by a solvent (e.g., water) that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

Acid Component

In some embodiments, the substrate comprises an acid component. The presence of either an acid component or an acid salt of nicotine in the substrate may improve the sensory attributes of the aerosol by reducing the harshness thereof, for example, when nicotine is present in the substrate. When present, the acid protonates the nicotine to form a nicotine salt in situ, either in the substrate or in the aerosol once it is formed. The presence of the nicotine salt results in an aerosol which some users find more satisfying. Further, the presence of the acid may reduce or substantially prevent evaporation of nicotine during preparation of the substrate (e.g., during drying), thereby reducing loss of nicotine during manufacturing.

The amount of acid present in the substrate may vary, for example, from 0% to about 20% by weight, based on the dry weight of the substrate. In some embodiments, the substrate comprises the acid in a ratio by moles to nicotine. In some embodiments, the molar ratio of nicotine to acid is 2.2:1 or less, such as 1.5:1 or less, or 1:1 or less. In some embodiments, the molar ratio of nicotine to acid is 0.5:1 or more.

In some embodiments, the acid comprises an acidic functional group which has a pKa value ranging from about 2 to about 6, for example from 3 to 6 or from 4 to 5, when measured at 25° C. In some embodiments, the acid may be a monoprotic acid, a diprotic acid, a triprotic acid, or a combination thereof.

In some embodiments, the acid is an organic acid. In some embodiments, the organic acid is a carboxylic acid. In some embodiments, the carboxylic acid comprises at least one carboxyl functional group. In some embodiments, the carboxylic acid is a mono-, a di-, or a tricarboxylic acid. In some embodiments, the carboxylic acid further comprises an alpha-hydroxy group. In some embodiments, the carboxylic acid further comprises a keto group.

In some embodiments, the carboxylic acid is selected from the group consisting of succinic acid, lactic acid, benzoic acid, citric acid, tartaric acid, fumaric acid, levulinic acid, acetic acid, malic acid, formic acid, sorbic acid, benzoic acid, propanoic acid, pyruvic acid, and combinations thereof. In some embodiments, the carboxylic acid is lactic acid. In some embodiments, the carboxylic acid is benzoic acid.

In other embodiments the acid is an inorganic acid. In some embodiments the inorganic acid is a mineral acid, such as sulfuric acid, hydrochloric acid, boric acid, phosphoric acid, or a combination thereof.

Other Components

In some embodiments, the substrate may further comprise a burn retardant material, conductive fibers or particles for heat conduction/induction, or any combination thereof. One example of a burn retardant material is ammonium phosphate. In some embodiments, other flame/burn retardant materials and additives may be included within the substrate, and may include organo-phosphorus compounds, borax, hydrated alumina, graphite, potassium, silica, tripolyphosphate, dipentaerythritol, pentaerythritol, and polyols. Other burn retardant materials, such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides may also be used. In each aspect of flame-retardant, burn-retardant, and/or scorch-retardant materials used in the substrate material and/or other components (whether alone or in combination with each other and/or other materials), the desirable properties are independent of and resistant to undesirable off-gassing or melting-type behavior. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

The substrate may also include conductive fibers or particles for heat conduction or heating by induction. In some embodiments, the conductive fibers or particles may be arranged in a substantially linear and parallel pattern. In some embodiments, the conductive fibers or particles may have a substantially random arrangement. In some embodiments, the conductive fibers or particles may be constructed of or more of an aluminum material, a stainless steel material, a copper material, a carbon material, and a graphite material. In some embodiments, one or more conductive fibers or particles with different Curie temperatures may be included in the substrate material to facilitate heating by induction at varying temperatures.

In still other implementations, the substrate material may comprise inorganic fibers of various types (e.g., fiber glass, metal wires/screens, etc.) and/or (organic) synthetic polymers. In various implementations, these “fibrous” materials could be unstructured (e.g., randomly distributed) or structured (e.g., a wire mesh).

Form of Substrate

The form of the substrate may vary. For example, the substrate may be in the form of a powder, a dust, particles, granules, pellets, shreds, strips, sheets, films, or the like. In some embodiments, the substrate is in shredded form, film form, paper form, or cast sheet form.

In some embodiments, the substrate is in the form of a cast sheet. In some embodiments, the cast sheet is a flat sheet. In some embodiments, the cast sheet has a thickness from about 0.015 mm to about 1.0 mm. Suitably, the thickness may be in the range of about 0.05 mm, 0.1 mm or 0.15 mm to about 0.5 mm or 0.3 mm, for example 0.1-3 mm or 0.15-3 mm. A sheet having a thickness of 0.2 mm may be particularly suitable. The thickness stipulated herein is a mean thickness for the sheet. In some cases, the sheet thickness may vary by no more than 25%, 20%, 15%, 10%, 5% or 1%.

In some embodiments, the flat sheet is layered, for example, in a series of overlapping layers 130 of the flat sheet 120 as illustrated in FIG. 4 and FIG. 5. In some embodiments, the flat sheet may be bunched, crumpled, crimped, and/or otherwise gathered layers. In some embodiments, the flat sheet may further be reduced into cut rag or strips for inserting into the substrate-containing segment of an aerosol delivery device. The flat sheet may also be gathered or rolled into rod for insertion into the substrate-containing segment of an aerosol delivery device. In some embodiments, the substrate is formed into a substantially cylindrical shape. In some embodiments, the flat sheet may be shredded. Although a sheet form of substrate is advantageous in the present disclosure, in certain embodiments, other forms could be utilized, such as beaded forms, shredded or particulate forms, and the like.

In some embodiments, an individual strip or piece of the substrate has a minimum thickness over its area of about 0.015 mm. In some cases, an individual strip or piece of the substrate has a minimum thickness over its area of about 0.05 mm or about 0.1 mm. In some cases, an individual strip or piece of the substrate has a maximum thickness over its area of about 1.0 mm. In some cases, an individual strip or piece of the substrate has a maximum thickness over its area of about 0.5 mm or about 0.3 mm.

In some examples, the substrate in sheet form may have a tensile strength of from around 150 N/m to around 3000 N/m, for instance from 150 N/m to 2500 N/m, or 150 N/m to 2000 N/m, or 200 N/m to 1700 N/m, or 250 N/m to 1500 N/m, or 200 N/m to 900 N/m. In some embodiments, the substrate may have a tensile strength of from 150 N/m to 500 N/m, or 200 N/m to 400 N/m, or 200 N/m to 300 N/m, or about 250 N/m. Such tensile strengths may be particularly suitable for embodiments wherein the substrate is formed as a sheet and then shredded and incorporated into an aerosol generating component.

In some embodiments, the substrate may have a tensile strength of from 150 N/m to 3000 N/m, for example 500 N/m to 1200 N/m, or from 600 N/m to 900 N/m, or from 700 N/m to 900 N/m, or around 800 N/m or greater. In some examples, the substrate may have a tensile strength of greater than 500 N/m, greater than 1000 N/m or greater than 1500 N/m. Such tensile strengths may be particularly suitable for embodiments wherein the substrate is included in an aerosol generating component as a rolled sheet, suitably in the form of a tube.

In some embodiments, the substrate is formed as a sheet and then cut into pieces, such as particles or shreds. The substrate material in such forms can be mixed with other materials as desired to form a blend, such as mixing with shredded or particulate tobacco materials or other non-tobacco substrate materials.

Preparation of Cast Sheets

In some embodiments, cast sheet technology may be used to make the substrate in the form of a flat sheet. The cast sheet generally comprises one or more fillers, one or more binders, optionally one or more aerosol formers, and optionally an active ingredient, a flavorant, or both, each as described herein. For example, in some embodiments the filler, at least a portion of the aerosol forming material as disclosed herein, and a binder may be blended together to form a slurry, which may be cast onto a surface (such as, for example, a moving belt). The cast slurry may then experience one or more drying and/or doctoring steps such that the result is a relatively consistent thickness cast sheet. Other examples of casting and paper-making techniques are set forth in U.S. Pat. No. 4,674,519 to Keritsis et al.; U.S. Pat. No. 4,941,484 to Clapp et al.; U.S. Pat. No. 4,987,906 to Young et al.; U.S. Pat. No. 4,972,854 to Kiernan et al.; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,706 to Kumar; the disclosures of which is incorporated herein by reference in their entireties. In some embodiments, the flat sheet may further be reduced into cut rag or strips for inserting into the substrate-containing segment of an aerosol delivery device. The cast sheet may also be gathered or rolled into rod for insertion into the substrate-containing segment of an aerosol delivery device. The cast sheet may be adhered or otherwise attached to a support.

The various components of the substrate may be contacted, combined, or mixed together using any mixing technique or equipment known in the art. Any mixing method that brings the substrate ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. Manners and methods for formulating mixtures will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

The sheets may optionally be dried to remove at least a portion of the liquid content (e.g., water). The final moisture content may be from about 8 to about 21% moisture by weight on a wet basis. Additionally, flavorants, extracts, aerosol forming materials, and the like can be added to the sheets after drying.

Substrate Loading

In various embodiments, loading of the substrate with the aerosol forming materials is achieved by impregnating the substrate with the aerosol forming materials during preparation of the substrate material, after formation, or both. In some embodiments, the slurry used e.g., in preparation of a cast sheet, includes the entire quantity of aerosol forming material. Alternatively, or in addition, a portion of the aerosol forming material may be added to the substrate post-formation (e.g., one or more aerosol forming materials may be sprayed or otherwise disposed in or on the substrate material in sheet form. In some embodiments, further aerosol forming materials may be impregnated in the substrate, either to the substrate forming slurry, or as a top dressing. Methods for loading aerosol forming materials onto substrate portions are described in U.S. Pat. No. 9,974,334 to Dooly et al., and U.S. Pub. Pat. App. Nos. 2015/0313283 to Collett et al. and 2018/0279673 to Sebastian et al., the disclosures of which are incorporated by reference herein in their entirety. As one of skill will recognize, multiple permutations of methods for loading the substrate with the aerosol forming materials is possible, depending on the specific substrate material, form, and the like. Accordingly, any such modifications are contemplated herein.

Aerosol Generating Components and Aerosol Delivery Devices

Substrates according to certain embodiments of the disclosure can be used in aerosol delivery devices or the aerosol generating components thereof. Accordingly, further example embodiments of the present disclosure relate to an aerosol delivery device comprising an aerosol generating component comprising the substrate as disclosed herein; a heat source configured to heat the aerosol forming materials carried in the substrate portion to form an aerosol; and an aerosol pathway extending from the aerosol generating component to a mouth-end of the aerosol delivery device. The individual components and construction of the aerosol generating component and aerosol delivery device are provided herein below.

Aerosol generating components of certain example aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example embodiments of the present disclosure can hold and use that component much like a smoker employs a traditional type of smoking article, draw on one end of that piece for inhalation of aerosol produced by that piece, take or draw puffs at selected intervals of time, and the like.

While the systems are generally described herein in terms of embodiments associated with aerosol delivery devices and/or aerosol generating components such as so-called "e-cigarettes" or "tobacco heating products," it should be understood that the mechanisms, components, features, and methods may be embodied in many different forms and associated with a variety of articles. For example, the description provided herein may be employed in conjunction with embodiments of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery devices by way of example only, and may be embodied and used in various other products and methods.

Aerosol delivery devices and/or aerosol generating components of the present disclosure may also be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like. The physical form of the inhalable substance is not necessarily limited by the nature of the inventive devices but rather may depend upon the nature of the medium and the inhalable substance itself as to whether it exists in a vapor state or an aerosol state. In some embodiments, the terms "vapor" and "aerosol" may be interchangeable. Thus, for simplicity, the terms "vapor" and "aerosol" as used to describe aspects of the disclosure are understood to be interchangeable unless stated otherwise.

More specific formats, configurations and arrangements of various substrate materials, aerosol generating components, and components within aerosol delivery devices of the present disclosure will be evident in light of the further disclosure provided hereinafter. Additionally, the selection of various aerosol delivery device components may be appreciated upon consideration of the commercially available electronic aerosol delivery devices. Further, the arrangement of the components within the aerosol delivery device may also be appreciated upon consideration of the commercially available electronic aerosol delivery devices.

Substrates according to certain embodiments of the disclosure can be used in aerosol generating components (e.g., segments) of heat-not-burn (HNB) devices. which use an ignitable heat source to heat a material (generally without combusting the material to any significant degree) to form an inhalable substance (e.g., carbon heated tobacco products). The material is typically heated without combusting the material to any significant degree. See, for example, US Patent App. Pub. Nos. 2017/0065000 to Sears et al.; 2015/0157052 to Ademe et al.; U.S. Pat. No. 10,314,330 to Conner et al.; U.S. Pat. No. 9,345,268 to Stone et al.; U.S. Pat. No. 9,149,072 to Conner et al.; U.S. Pat. Nos. 5,105,831 and 5,042,509, both to Banerjee et al., each of which is incorporated herein by reference. Components of such systems have the form of articles that are sufficiently compact to be considered hand-held devices. That is, use of components of certain example aerosol delivery devices does not result in the production of smoke in the sense that aerosol results principally from by-products of combustion or pyrolysis of tobacco, but rather, use of those systems results in the production of vapors resulting from volatilization or vaporization of certain components incorporated therein.

Accordingly, in some embodiments, aerosol generating components of the present disclosure may generally include an ignitable heat source configured to heat a substrate material as disclosed herein to aerosolize an aerosol forming material associated with the substrate material, forming an inhalable substance. The substrate material and/or at least a portion of the heat source may be covered in an outer wrap, or wrapping, a casing, a component, a module, a member, or the like. The overall design of the enclosure is variable, and the format or configuration of the enclosure that defines the overall size and shape of the aerosol generating component is also variable. Although other configurations are possible, it may be desirable, in some aspects, that the overall design, size, and/or shape of these embodiments resemble that of a conventional cigarette or cigar.

Substrates according to certain embodiments of the disclosure can be used in aerosol generating components of aerosol delivery devices which use electrical energy to heat a substrate material as disclosed herein to aerosolize an aerosol forming material associated with the substrate material, forming an inhalable substance (e.g., electrically heated tobacco products). In some example embodiments, the aerosol delivery devices may be characterized as electronic cigarettes. Accordingly, in some embodiments, aerosol delivery devices of the present disclosure may comprise some combination of a power source (e.g., an electrical power source), at least one control component (e.g., means for actuating, controlling, regulating and ceasing power for heat generation, such as by controlling electrical current flow from the power source to other components of the article, e.g., a microprocessor, individually or as part of a microcontroller), a heat source (e.g., an electrical resistance heating element or other component and/or an inductive coil or other associated components and/or one or more radiant heating elements), and an aerosol generating component that includes a substrate portion as disclosed herein, capable of yielding an aerosol upon application of sufficient heat. Note that it is possible to physically combine one or more of the above-noted components. For instance, in certain embodiments, a conductive heater trace can be printed on the surface of a substrate material as described herein (e.g., a sheet or film) using a conductive ink such that the heater trace can be powered by the power source and used as the resistance heating element. Example conductive inks include graphene inks and inks containing various metals, such as inks including silver, gold, palladium, platinum, and alloys or other combinations thereof (e.g., silver-palladium or silver-platinum inks), which can be printed on a surface using processes such as gravure printing, flexographic printing, off-set printing, screen printing, ink-jet printing, or other appropriate printing methods.

In various embodiments, a number of these components may be provided within an outer body or shell, which, in some embodiments, may be referred to as a housing. The overall design of the outer body or shell may vary, and the format or configuration of the outer body that may define the overall size and shape of the aerosol delivery device may vary. Although other configurations are possible, in some embodiments an elongated body resembling the shape of a cigarette or cigar may be a formed from a single, unitary housing or the elongated housing can be formed of two or more separable bodies. For example, an aerosol delivery device may comprise an elongated shell or body that may be substantially tubular in shape and, as such, resemble the shape of a conventional cigarette or cigar. In one example, all of the components of the aerosol delivery device are contained within one housing or body. In other embodiments, an aerosol delivery device may comprise two or more housings that are joined and are separable. For example, an aerosol delivery device may possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing aerosol generating component).

Aerosol generating components and aerosol delivery devices comprising the substrate as disclosed herein, and using either heat from combustion or heat from electrical energy, may further comprise additional materials, e.g., in admixture with the substrate, such as tobacco materials, tobacco-derived materials, and the like, referred to herein as "aerosol-generating materials." Such aerosol generating components may also be referred to herein as "consumables", meaning articles comprising or consisting of a substrate as described herein, part or all of which are intended to be consumed during use by a user.

In some embodiments, the aerosol generating component comprises the substrate as disclosed herein in the form of a sheet, or in the form of shreds. In some embodiments, the aerosol generating component further comprises an aerosol-generating material, such as a tobacco material or a tobacco-derived material. In some embodiments, the aerosol-generating material is a tobacco material in the form of strips or particles, and is blended with the substrate. In some embodiments, both the substrate and the tobacco material are in the form of strips. In some embodiments, the substrate is present in a layered form, comprising multiple sheets (layers) of substrate.

In some embodiments, the aerosol generating component further comprises a support. In some embodiments, the substrate is attached or adhered to the support. In some embodiments, the support is planar. A non-limiting embodiment of an aerosol generating component comprising a support and having a substrate attached or adhered thereto is illustrated in FIG. 1. With reference to FIG. 1, an aerosol generating component 10 includes a support 20 and a substrate 30 disposed thereon.

The support 20 may be at least partially porous in the region of a surface abutting the substrate 30. Conversely, the surface of the support 20 facing away from the substrate 30 may be arranged in contact with a heat source as described herein. In some embodiments, the support 20 may be a laminate structure. For example, the support 20 may comprise a cardboard-backed foil, where the cardboard layer abuts the substrate 30. A foil backing is substantially impermeable, providing control of the aerosol flow path. A metal foil backing may also serve to conduct heat to the substrate 30. In some embodiments, the foil layer of the cardboard-backed foil abuts the substrate 30. The foil is substantially impermeable, thereby preventing moisture in the substrate 30 from being absorbed into the cardboard, which could weaken its structural integrity. In some embodiments, the support 20 is formed from or comprises metal foil, such as aluminum foil. A metallic support may allow for better conduction of thermal energy to the substrate. Additionally, or alternatively, a metal foil may function as a susceptor in an induction heating system. In particular embodiments, the support 20 comprises a metal foil layer and a support layer, such as cardboard. In these embodiments, the metal foil layer may have a thickness of less than 20 μm, such as from about 1 μm to about 10 μm, suitably about 5 μm.

Aerosol generating components and aerosol delivery devices comprising the substrate as disclosed herein, and using either heat from combustion or heat from electrical energy to provide an aerosol therefrom, are described further herein below with reference to FIGS. 2-7.

In this regard, FIG. 2 illustrates an aerosol delivery device 100 according to an example embodiment of the present disclosure. The aerosol delivery device 100 may include a control body 102 and an aerosol generating component 104. In some embodiments, the aerosol generating component is configured for use with a conductive and/or inductive heat source to heat a substrate material to form an aerosol. In various embodiments, a conductive heat source may comprise a heating assembly that comprises a resistive heating member. Resistive heating members may be configured to produce heat when an electrical current is directed therethrough. Electrically conductive materials useful as resistive heating members may be those having low mass, low density, and moderate resistivity and that are thermally stable at the temperatures experienced during use. Useful heating members heat and cool rapidly, and thus provide for the efficient use of energy. Rapid heating of the member may be beneficial to provide almost immediate volatilization of an aerosol forming materials in proximity thereto. Rapid cooling prevents substantial volatilization (and hence waste) of the aerosol forming materials during periods when aerosol formation is not desired. Such heating members may also permit relatively precise control of the temperature range experienced by the aerosol forming materials, especially when time based current control is employed. Useful electrically conductive materials are typically chemically non-reactive with the materials being heated (e.g., aerosol forming materials and other inhalable substance materials) so as not to adversely affect the flavor or content of the aerosol or vapor that is produced. Some example, non-limiting, materials that may be used as the electrically conductive material include carbon, graphite, carbon/graphite composites, metals, ceramics such as metallic and non-metallic carbides, nitrides, oxides, silicides, inter-metallic compounds, cermets, metal alloys, and metal foils. In particular, refractory materials may be useful. Various, different materials can be mixed to achieve the desired properties of resistivity, mass, and thermal conductivity. In specific embodiments, metals that can be utilized include, for example, nickel, chromium, alloys of nickel and chromium (e.g., nichrome), and steel. Materials that can be useful for providing resistive heating are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties.

In various embodiments, a heating member may be provided in a variety of forms, such as in the form of a foil, a foam, a mesh, a hollow ball, a half ball, discs, spirals, fibers, wires, films, yarns, strips, ribbons, or cylinders. Such heating members often comprise a metal material and are configured to produce heat as a result of the electrical resistance associated with passing an electrical current therethrough. Such resistive heating members may be positioned in proximity to, and/or in direct contact with, the substrate portion. For example, in one embodiment, a heating member may comprise a cylinder or other heating device located in the control body 102, wherein the cylinder is constructed of one or more conductive materials, including, but not limited to, copper, aluminum, platinum, gold, silver, iron, steel, brass, bronze, carbon (e.g., graphite), or any combination thereof. In various embodiments, the heating member may also be coated with any of these or other conductive materials. The heating member may be located proximate an engagement end of the control body 102, and may be configured to substantially surround a portion of the heated end 106 of the aerosol generating component 104 that includes the substrate portion 110. In such a manner, the heating member may be located proximate the substrate portion 110 of the aerosol generating component 104 when the aerosol generating component 104 is inserted into the control body 102. In other examples, at least a portion of a heating member may penetrate at least a portion of an aerosol generating component (such as, for example, one or more prongs and/or spikes that penetrate an aerosol generating component), when the aerosol generating component is inserted into the control body. Although in some embodiments the heating member may comprise a cylinder, it should be noted that in other embodiments, the heating member may take a variety of forms and, in some embodiments, may make direct contact with and/or penetrate the substrate portion. As described above, in addition to being configured for use with a conductive heat source, the presently disclosed aerosol generating component may also be configured for use with an inductive heat source to heat a substrate portion to form an aerosol. In various embodiments, an inductive heat source may comprise a resonant transformer, which may comprise a resonant transmitter and a resonant receiver (e.g., a susceptor). In some embodiments, the resonant transmitter and the resonant receiver may be located in the control body 102. In other embodiments, the resonant receiver, or a portion thereof, may be located in the aerosol generating component 104. For example, in some embodiments, the control body 102 may include a resonant transmitter, which, for example, may comprise a foil material, a coil, a cylinder, or other structure configured to generate an oscillating magnetic field, and a resonant receiver, which may comprise one or more prongs that extend into the substrate portion or are surrounded by the substrate portion. In some embodiments, the aerosol generating component is in intimate contact with the resonant receiver.

In other embodiments, a resonant transmitter may comprise a helical coil configured to circumscribe a cavity into which an aerosol generating component, and in particular, a substrate portion of an aerosol generating component, is received. In some embodiments, the helical coil may be located between an outer wall of the device and the receiving cavity. In one embodiment, the coil winds may have a circular cross section shape; however, in other embodiments, the coil winds may have a variety of other cross section shapes, including, but not limited to, oval shaped, rectangular shaped, L-shaped, T-shaped, triangular shaped, and combinations thereof. In another embodiment, a pin may extend into a portion of the receiving cavity, wherein the pin may comprise the resonant transmitter, such as by including a coil structure around or within the pin. In various embodiments, an aerosol generating component may be received in the receiving cavity wherein one or more components of the aerosol generating component may serve as the resonant receiver. In some embodiments, the aerosol generating component comprises the resonant receiver. Other possible resonant transformer components, including resonant transmitters and resonant receivers, are described in U.S. Pat. App. Pub. No. 2019/0124979 to Sebastian et al., which is incorporated herein by reference in its entirety.

In various embodiments, the aerosol generating component 104 and the control body 102 may be permanently or detachably aligned in a functioning relationship. In this regard, FIG. 2 illustrates the aerosol delivery device 100 in a coupled configuration, whereas FIG. 2 illustrates the aerosol delivery device 100 in a decoupled configuration. Various mechanisms may connect the aerosol generating component 104 to the control body 102 to result in a threaded engagement, a press-fit engagement, an interference fit, a sliding fit, a magnetic engagement, or the like.

In various embodiments, the aerosol delivery device 100 according to an example embodiment of the present disclosure may have a variety of overall shapes, including, but not limited to an overall shape that may be defined as being substantially rod-like or substantially tubular shaped or substantially cylindrically shaped. In the embodiments of FIGS. 2-3, the device 100 has a substantially round cross-section; however, other cross-sectional shapes (e.g., oval, square, triangle, etc.) also are encompassed by the present disclosure. For example, in some embodiments one or both of the control body 102 or the aerosol generating component 104 (and/or any subcomponents) may have a substantially rectangular shape, such as a substantially rectangular cuboid shape (e.g., similar to a USB flash drive). In other embodiments, one or both of the control body 102 or the aerosol generating component 104 (and/or any subcomponents) may have other hand-held shapes. For example, in some embodiments the control body 102 may have a small box shape, various pod mod shapes, or a fob-shape. Thus, such language that is descriptive of the physical shape of the article may also be applied to the individual components thereof, including the control body 102 and the aerosol generating component 104.

Alignment of the components within the aerosol delivery device of the present disclosure may vary across various embodiments. In some embodiments, the substrate portion may be positioned proximate a heat source so as to maximize aerosol delivery to the user. Other configurations, however, are not excluded. Generally, the heat source may be positioned sufficiently near the substrate portion so that heat from the heat source can volatilize the substrate portion (e.g., the aerosol forming material therein) and form an aerosol for delivery to the user. When the heat source heats the substrate portion, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device 100 of various embodiments may incorporate a battery and/or other electrical power source to provide current flow sufficient to provide various functionalities to the aerosol delivery device, such as powering of the heat source, powering of control systems, powering of indicators, and the like. As will be discussed in more detail below, the power source may take on various embodiments. The power source may be able to deliver sufficient power to rapidly activate the heat source to provide for aerosol formation and power the aerosol delivery device through use for a desired duration of time. In some embodiments, the power source is sized to fit conveniently within the aerosol delivery device so that the aerosol delivery device can be easily handled. Examples of useful power sources include lithium-ion batteries that are typically rechargeable (e.g., a rechargeable lithium-manganese dioxide battery). In particular, lithium polymer batteries can be used as such batteries can provide increased safety. Other types of batteries—e.g., N50-AAA CADNICA nickel-cadmium cells—may also be used. Additionally, an example power source is of a sufficiently light weight to not detract from a desirable smoking experience. Some examples of possible power sources are described in U.S. Pat. No. 9,484,155 to Peckerar et al., and U.S. Pat. App. Pub. No. 2017/0112191 to Sur et al., the disclosures of which are incorporated herein by reference in their respective entireties.

In specific embodiments, one or both of the control body 102 and the aerosol generating component 104 may be referred to as being disposable or as being reusable. For example, the control body 102 may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some embodiments, the aerosol generating component 104 may comprise a single-use device. A single use component for use with a control body is disclosed in U.S. Pat. No. 8,910,639 to Chang et al., which is incorporated herein by reference in its entirety.

In further embodiments, the power source may also comprise a capacitor. Capacitors are capable of discharging more quickly than batteries and can be charged between puffs, allowing the battery to discharge into the capacitor at a lower rate than if it were used to power the heat source directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor.

Further components may be utilized in the aerosol delivery device of the present disclosure. For example, the aerosol delivery device may include a flow sensor that is sensitive either to pressure changes or air flow changes as the consumer draws on the article (e.g., a puff-actuated switch). Other possible current actuation/deactuation mechanisms may include a temperature actuated on/off switch or a lip pressure actuated switch. An example mechanism that can provide such puff-actuation capability includes a Model 163PC01D36 silicon sensor, manufactured by the MicroSwitch division of Honeywell, Inc., Freeport, Ill. Representative flow sensors, current regulating components, and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference is also made to the control schemes described in U.S. Pat. No. 9,423,152 to Ampolini et al., which is incorporated herein by reference in its entirety.

In another example, an aerosol delivery device may comprise a first conductive surface configured to contact a first body part of a user holding the device, and a second conductive surface, conductively isolated from the first conductive surface, configured to contact a second body part of the user. As such, when the aerosol delivery device detects a change in conductivity between the first conductive surface and the second conductive surface, a vaporizer is activated to vaporize a substance so that the vapors may be inhaled by the user holding unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory. Reference is made to U.S. Pat. No. 9,861,773 to Terry et al., which is incorporated herein by reference in its entirety.

In addition, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present device include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. 2017/0099877 to Worm et al. discloses capsules that may be included in aerosol delivery devices and fob-shape configurations for aerosol delivery devices, and is incorporated herein by reference in its entirety. A variety of the materials disclosed by the foregoing documents may be incorporated into the present devices in various embodiments, and all of the foregoing disclosures are incorporated herein by reference in their entireties.

Referring to FIG. 3, in the depicted embodiment, the aerosol generating component 104 comprises a heated end 106, which is configured to be inserted into the control body 102, and a mouth end 108, upon which a user draws to create the aerosol. At least a portion of the heated end 106 includes a substrate portion 110. In some embodiments, the substrate portion 110 comprises a substrate comprising the aerosol forming material, each as disclosed herein. In various embodiments, the aerosol generating component 104, or a portion thereof, may be wrapped in an exterior overwrap material 112. In various embodiments, the mouth end 108 of the aerosol generating component 104 may include a filter 114, which may, for example, be made of a cellulose acetate or polypropylene material. The filter 114 may additionally or alternatively contain strands of tobacco containing material, such as described in U.S. Pat. No. 5,025,814 to Raker et al., which is incorporated herein by reference in its entirety. In various embodiments, the filter 114 may increase the structural integrity of the mouth end of the aerosol generating component 104, and/or provide filtering capacity, if desired, and/or provide resistance to draw. In some embodiments, the filter may comprise discrete segments. For example, some embodiments may include a segment providing filtering, a segment providing draw resistance, a hollow segment providing a space for the aerosol to cool, a segment providing increased structural integrity, other filter segments, and any one or any combination of the above.

In some embodiments, the material of the exterior overwrap 112 may comprise a material that resists transfer of heat, which may include a paper or other fibrous material, such as a cellulose material. The exterior overwrap material may also include at least one filler material imbedded or dispersed within the fibrous material. In various embodiments, the filler material may have the form of water insoluble particles. Additionally, the filler material may incorporate inorganic components. In various embodiments, the exterior overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The exterior overwrap may also include a material typically used in a filter element of a conventional cigarette, such as cellulose acetate. Further, an excess length of the exterior overwrap at the mouth end 108 of the aerosol generating component may function to simply separate the substrate portion 110 from the mouth of a consumer or to provide space for positioning of a filter material, as described below, or to affect draw on the article or to affect flow characteristics of the vapor or aerosol leaving the device during draw. Further discussions relating to the configurations for exterior overwrap materials that may be used with the present disclosure may be found in U.S. Pat. No. 9,078,473 to Worm et al., which is incorporated herein by reference in its entirety.

Although in some embodiments an aerosol generating component and a control body may be provided together as a complete aerosol delivery article generally, the components may be provided separately. For example, the present disclosure also encompasses a disposable unit for use with a reusable smoking article or a reusable pharmaceutical delivery article. In specific embodiments, such a disposable unit (which may be an aerosol generating component as illustrated in the appended figures) can comprise a substantially tubular shaped body having a heated end configured to engage the reusable aerosol delivery article, an opposing mouth end configured to allow passage of an inhalable substance to a consumer, and a wall with an outer surface and an inner surface that defines an interior space. Various embodiments of an aerosol generating component (or cartridge) are described in U.S. Pat. No. 9,078,473 to Worm et al., which is incorporated herein by reference in its entirety.

Although some figures described herein illustrate the control body and aerosol generating component in a working relationship, it is understood that the control body and the aerosol generating component may exist as individual devices. Accordingly, any discussion otherwise provided herein in relation to the components in combination also should be understood as applying to the control body and the aerosol generating component as individual and separate components.

In another aspect, the present disclosure may be directed to kits that provide a variety of components as described herein. For example, a kit may comprise a control body with one or more aerosol generating components. A kit may further comprise a control body with one or more charging components. A kit may further comprise a control body with one or more batteries. A kit may further comprise a control body with one or more aerosol generating components and one or more charging components and/or one or more batteries. In further embodiments, a kit may comprise a plurality of aerosol generating components. A kit may further comprise a plurality of aerosol generating components and one or more batteries and/or one or more charging components. In the above embodiments, the aerosol generating components or the control bodies may be provided with a heating member inclusive thereto. The inventive kits may further include a case (or other packaging, transporting, or storage component) that accommodates one or more of the further kit components. The case could be a reusable hard or soft container. Further, the case could be simply a box or other packaging structure.

FIG. 4 illustrates a perspective schematic view of an aerosol generating component according to an example embodiment of the disclosure. In particular, FIG. 4 illustrates the aerosol generating component 104 having a substrate portion 110 that comprises a series of overlapping layers 130 of a substrate in sheet form 120. With reference to the description above, in the depicted embodiment, the substrate sheet 120 comprises a film or layer as disclosed herein. In various embodiments, the term "overlapping layers" may also include bunched, crumpled, crimped, and/or otherwise gathered layers in which the individual layers may not be obvious.

For example, FIG. 5 illustrates a schematic cross-section drawing of a substrate portion 110 of an aerosol generating component 104 according to an example embodiment of the present disclosure. In particular, FIG. 5 illustrates the substrate portion 110, which comprises a series of overlapping layers 130 of the substrate sheet 120. In the depicted embodiment, at least a portion of the overlapping layers 130 is substantially surrounded about its outer surface with a first cover layer 132. In various embodiments, the first cover layer 132 may be constructed via a casting process, such as that described in U.S. Pat. No. 5,697,385 to Seymour et al., the disclosure of which is incorporated herein by reference in its entirety.

In the depicted embodiment, at least a portion of the overlapping layers 130 and the first cover layer 132 are substantially surrounded about an outer surface with a second cover layer 134. Although the composition of the second cover layer 134 may vary, in the depicted embodiment the second cover layer 134 comprises a metal foil material, such as an aluminum foil material. In other embodiments, the second cover layer may comprise other materials, including, but not limited to, a copper material, a tin material, a gold material, an alloy material, a ceramic material, or other thermally conductive amorphous carbon-based material, and/or any combinations thereof. The depicted embodiment further includes a third cover layer 136, which substantially surrounds the overlapping layers 130, first cover layer 132, and the second cover layer 134, about an outer surface thereof. In the depicted embodiment, the third cover layer 136 comprises a paper material, such as a conventional cigarette wrapping paper. In various embodiments, the paper material may comprise rag fibers, such as non-wood plant fibers, and may include flax, hemp, sisal, rice straw, and/or esparto fibers.

In various embodiments, other components may exist between the substrate portion 110 and the mouth end 108 of the aerosol generating component 104. For example, in some embodiments one or any combination of the following may be positioned between the substrate portion 110 and the mouth end 108 of the aerosol generating component 104: an air gap; a hollow tube structure; phase change materials for cooling air; flavor releasing media; ion exchange fibers capable of selective chemical adsorption; aerogel particles as filter medium; and other suitable materials. Some examples of possible phase change materials include, but are not limited to, salts, such as $AgNO_3$, $AlCl_3$, $TaCl_3$, $InCl_3$, $SnCl_2$, $AlI_3$, and $TiI_4$; metals and metal alloys such as selenium, tin, indium, tin-zinc, indium-zinc, or indium-bismuth; and organic compounds such as D-mannitol, succinic acid, p-nitrobenzoic acid, hydroquinone and adipic acid. Other examples are described in U.S. Pat. No. 8,430,106 to Potter et al., which is incorporated herein by reference in its entirety.

FIG. 6 illustrates a perspective view of an aerosol generating component, according to another example embodiment of the present disclosure, and FIG. 7 illustrates a perspective view of the aerosol generating component of FIG. 5 with an outer wrap removed. In particular, FIG. 6 illustrates an aerosol generating component 200 that includes an outer wrap 202, and FIG. 7 illustrates the aerosol generating component 200 wherein the outer wrap 202 is removed to reveal the other components of the aerosol generating component 200. In the depicted embodiment, the aerosol generating component 200 of the depicted embodiment includes a heat source 204, a substrate portion 210, an intermediate component 208, and a filter 212. In the depicted embodiment, the intermediate component 208 and the filter 212 together comprise a mouthpiece 214.

In various embodiments, the heat source 204 may be configured to generate heat upon ignition thereof. In the depicted embodiment, the heat source 204 comprises a combustible fuel element that has a generally cylindrical shape and that incorporates a combustible carbonaceous material. In other embodiments, the heat source 204 may have a different shape, for example, a prism shape having a triangular, cubic or hexagonal cross-section. Carbonaceous materials generally have a high carbon content. Certain example carbonaceous materials may be composed predominately of carbon, and/or typically may have carbon contents of greater than about 60 percent, generally greater than about 70 percent, often greater than about 80 percent, and frequently greater than about 90 percent, on a dry weight basis.

In some instances, the heat source 204 may incorporate elements other than combustible carbonaceous materials (e.g., tobacco components, such as powdered tobaccos or tobacco extracts; flavoring agents; salts, such as sodium chloride, potassium chloride and sodium carbonate; heat stable graphite fibers; iron oxide powder; glass filaments; powdered calcium carbonate; alumina granules; ammonia sources, such as ammonia salts; binding agents, such as guar gum, ammonium alginate and sodium alginate; and/or phase change materials for lowering the temperature of the heat source, described herein above). Although specific dimensions of an applicable heat source may vary, in some embodiments, the heat source 204 may have a length in an inclusive range of approximately 7 mm to approximately 20 mm, and in some embodiments may be approximately 17 mm, and an overall diameter in an inclusive range of approximately 3 mm to approximately 8 mm, and in some embodiments may be approximately 4.8 mm (and in some embodiments, approximately 7 mm). Although in other embodiments, the heat source may be constructed in a variety of ways, in the depicted embodiment, the heat source 204 is extruded or compounded using a ground or powdered carbonaceous material, and has a density that is greater than about 0.5 $g/cm^3$, often greater than about 0.7 $g/cm^3$, and frequently greater than about 1 $g/cm^3$, on a dry weight basis. See, for example, the types of fuel source components, formulations and designs set forth in U.S. Pat. No. 5,551,451 to Riggs et al. and U.S. Pat. No. 7,836,897 to Borschke et al., which are incorporated herein by reference in their entireties. Although in various embodiments, the heat source may have a variety of forms, including, for example, a substantially solid cylindrical shape or a hollow cylindrical (e.g., tube) shape, the heat source 204 of the depicted embodiment comprises an extruded monolithic carbonaceous material that has a generally cylindrical shape but with a plurality of grooves 216 extending longitudinally from a first end of the extruded monolithic carbonaceous material to an opposing second end of the extruded monolithic carbonaceous material. In some embodiments, the aerosol delivery device, and in particular, the heat source, may include a heat transfer component. In various embodiments, a heat transfer component may be proximate the heat source, and, in some embodiments, a heat transfer component may be located in or within the heat source. Some examples of heat transfer components are described in in U.S. Pat. App. Pub. No. 2019/0281891 to Hejazi et al., which is incorporated herein by reference in its entirety.

Although in the depicted embodiment, the grooves 216 of the heat source 204 are substantially equal in width and depth and are substantially equally distributed about a circumference of the heat source 204, other embodiments may include as few as two grooves, and still other embodiments may include as few as a single groove. Still other embodiments may include no grooves at all. Additional embodiments may include multiple grooves that may be of unequal width and/or depth, and which may be unequally spaced around a circumference of the heat source. In still other embodiments, the heat source may include flutes and/or slits extending longitudinally from a first end of the extruded monolithic carbonaceous material to an opposing second end thereof. In some embodiments, the heat source may comprise a foamed carbon monolith formed in a foam process of the type disclosed in U.S. Pat. No. 7,615,184 to Lobovsky, which is incorporated herein by reference in its entirety. As such, some embodiments may provide advantages with regard to reduced time taken to ignite the heat source. In some other embodiments, the heat source may be co-extruded with a layer of insulation (not shown), thereby reducing manufacturing time and expense. Other embodiments of fuel elements include carbon fibers of the type described in U.S. Pat. No. 4,922,901 to Brooks et al. or other heat source embodiments such as is disclosed in U.S. Pat. App. Pub. No. 2009/0044818 to Takeuchi et al., each of which is incorporated herein by reference in its entirety.

Generally, the heat source is positioned sufficiently near a substrate portion carrying one or more aerosol forming materials so that the aerosol formed/volatilized by the application of heat from the heat source to the aerosol forming materials (as well as any flavorants, medicaments, and/or the like that are likewise provided for delivery to a user) is deliverable to the user by way of the mouthpiece. That is, when the heat source heats the substrate portion, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

Referring back to FIGS. 6 and 7, the outer wrap 202 may be provided to engage or otherwise join together at least a portion of the heat source 204 with the substrate portion 210 and at least a portion of the mouthpiece 214. In various embodiments, the outer wrap 202 is configured to be retained in a wrapped position in any manner of ways including via an adhesive, or a fastener, and the like, to allow the outer wrap 202 to remain in the wrapped position. Otherwise, in some other aspects, the outer wrap 202 may be configured to be removable as desired. For example, upon retaining the outer wrap 202 in a wrapped position, the outer wrap 202 may be able to be removed from the heat source 204, the substrate portion 210, and/or the mouthpiece 214.

In some embodiments, in addition to the outer wrap 202, the aerosol delivery device may also include a liner that is configured to circumscribe the substrate portion 210 and at least a portion of the heat source 204. Although in other embodiments the liner may circumscribe only a portion of the length of the substrate portion 210, in some embodiments, the liner may circumscribe substantially the full length of the substrate portion 210. In some embodiments, the outer wrap material 202 may include the liner. As such, in some embodiments the outer wrap material 202 and the liner may be separate materials that are provided together (e.g., bonded, fused, or otherwise joined together as a laminate). In other embodiments, the outer wrap 202 and the liner may be the same material. In any event, the liner may be configured to thermally regulate conduction of the heat generated by the ignited heat source 204, radially outward of the liner. As such, in some embodiments, the liner may be constructed of a metal foil material, an alloy material, a ceramic material, or other thermally conductive amorphous carbon-based material, and/or an aluminum material, and in some embodiments may comprise a laminate. In some embodiments, depending on the material of the outer wrap 202 and/or the liner, a thin layer of insulation may be provided radially outward of the liner. Thus, the liner may advantageously provide, in some aspects, a manner of engaging two or more separate components of the aerosol generating component 200 (such as, for example, the heat source 204, the substrate portion 210, and/or a portion of the mouthpiece 214), while also providing a manner of facilitating heat transfer axially therealong, but restricting radially outward heat conduction.

As shown in FIG. 6, the outer wrap 202 (and, as necessary, the liner, and the substrate portion 210) may also include one or more openings formed therethrough that allow the entry of air upon a draw on the mouthpiece 214. In various embodiments, the size and number of these openings may vary based on particular design requirements. In the depicted embodiment, a plurality of openings 220 are located proximate an end of the substrate portion 210 closest to the heat source 204, and a plurality of separate cooling openings 221 are formed in the outer wrap 202 (and, in some embodiments, the liner) in an area proximate the filter 212 of the mouthpiece 214. Although other embodiments may differ, in the depicted embodiment, the openings 220 comprise a plurality of openings substantially evenly spaced about the outer surface of the aerosol generating component 200, and the openings 221 also comprise a plurality of openings substantially evenly spaced around the outer surface of the aerosol generating component 200. Although in various embodiments the plurality of openings may be formed through the outer wrap 202 (and, in some embodiments, the liner) in a variety of ways, in the depicted embodiment, the plurality of openings 220 and the plurality of separate cooling openings 221 are formed via laser perforation.

Referring back to FIG. 7, the aerosol generating component 200 of the depicted implementation also includes an intermediate component 208 and at least one filter 212. It should be noted that in various implementations, the intermediate component 208 or the filter 212, individually or together, may be considered a mouthpiece 214 of the aerosol generating component 200. Although in various implementations, neither the intermediate component nor the filter need be included, in the depicted implementation the intermediate component 208 comprises a substantially rigid member that is substantially inflexible along its longitudinal axis. In the depicted implementation, the intermediate component 208 comprises a hollow tube structure, and is included to add structural integrity to the aerosol generating component 200 and provide for cooling the produced aerosol. In some implementations, the intermediate component 208 may be used as a container for collecting the aerosol. In various implementations, such a component may be constructed from any of a variety of materials and may include one or more adhesives. Example materials include, but are not limited to, paper, paper layers, paperboard, plastic, cardboard, and/or composite materials. In the depicted implementation, the intermediate component 208 comprises a hollow cylindrical element constructed of a paper or plastic material (such as, for example, ethyl vinyl acetate (EVA), or other polymeric materials such as poly ethylene, polyester, silicone, etc. or ceramics (e.g., silicon carbide, alumina, etc.), or other acetate fibers), and the filter comprises a packed rod or cylindrical disc constructed of a gas permeable material (such as, for example, cellulose acetate or fibers such as paper or rayon, or polyester fibers).

As noted, in some implementations the mouthpiece 214 may comprise a filter 212 configured to receive the aerosol therethrough in response to the draw applied to the mouthpiece 214. In various implementations, the filter 212 is provided, in some aspects, as a circular disc radially and/or longitudinally disposed proximate the second end of the intermediate component 208. In this manner, upon draw on the mouthpiece 214, the filter 212 receives the aerosol flowing through the intermediate component 208 of the aerosol generating component 200. In some implementations, the filter 212 may comprise discrete segments. For example, some implementations may include a segment providing filtering, a segment providing draw resistance, a hollow segment providing a space for the aerosol to cool, a segment providing increased structural integrity, other filter segments, and any one or any combination of the above. In some implementations, the filter 212 may additionally or alternatively contain strands of tobacco containing material, such as described in U.S. Pat. No. 5,025,814 to Raker et al., which is incorporated herein by reference in its entirety.

In various implementations the size and shape of the intermediate component 208 and/or the filter 212 may vary, for example the length of the intermediate component 208 may be in an inclusive range of approximately 10 mm to approximately 30 mm, the diameter of the intermediate component 208 may be in an inclusive range of approximately 3 mm to approximately 8 mm, the length of the filter 212 may be in an inclusive range of approximately 10 mm to approximately 20 mm, and the diameter of the filter 212 may be in an inclusive range of approximately 3 mm to approximately 8 mm. In the depicted implementation, the intermediate component 208 has a length of approximately 20 mm and a diameter of approximately 4.8 mm (and in some implementations, approximately 7 mm), and the filter 212 has a length of approximately 15 mm and a diameter of approximately 4.8 mm (or in some implementations, approximately 7 mm).

In various implementations, ignition of the heat source 204 results in aerosolization of the aerosol forming materials associated with the substrate portion 210. In certain embodiments, the elements of the substrate portion 210 do not experience thermal decomposition (e.g., charring, scorching, or burning) to any significant degree, and the aerosolized components are entrained in the air that is drawn through the aerosol generating component 200, including the filter 212, and into the mouth of the user. In various implementations, the mouthpiece 214 (e.g., the intermediate component 208 and/or the filter 212) is configured to receive the generated aerosol therethrough in response to a draw applied to the mouthpiece 214 by a user. In some implementations, the mouthpiece 214 may be fixedly engaged to the substrate portion 210. For example, an adhesive, a bond, a weld, and the like may be suitable for fixedly engaging the mouthpiece 214 to the substrate portion 210. In one example, the mouthpiece 214 is ultrasonically welded and sealed to an end of the substrate portion 210.

Although an aerosol deliver device and/or an aerosol generating component according to the present disclosure may take on a variety of embodiments, as discussed in detail above, the use of the aerosol delivery device and/or aerosol generating component by a consumer will be similar in scope. The foregoing description of use of the aerosol delivery device and/or aerosol generating component is applicable to the various embodiments described through minor modifications, which are apparent to the person of skill in the art in light of the further disclosure provided herein. The description of use, however, is not intended to limit the use of the articles of the present disclosure but is provided to comply with all necessary requirements of disclosure herein.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

EXAMPLES

Aspects of the present invention are more fully illustrated by the following examples, which are set forth to illustrate certain aspects of the present invention and are not to be construed as limiting thereof.

Example 1. Cast Sheet Substrate Comprising Microcrystalline Cellulose

An example of a cast sheet substrate embodiment of the disclosure was prepared according to the formula provided in Table 1. The actual ingredients and percentages can be varied depending on the desired properties of the final product.

Water and carboxymethylcellulose binder were mixed in a high shear mixer (e.g., a kitchen blender) in amounts sufficient to make a 2-3% binder solution by weight. The mixer was charged with water and set at low to medium speed. The carboxymethylcellulose was added and the suspension mixed until complete dispersion or dissolution occurred. The mixing speed was increased and mixing continued for another 10-15 minutes. The wood pulp was added, and mixing continued at high speed for another 5 minutes. The speed was reduced and microcrystalline cellulose was slowly added. Mixing was continued for about 5 to 6 minutes until all microcrystalline cellulose was dispersed. Glycerol was added and mixing continued for another 5 minutes at medium speed to obtain the final slurry. The final slurry was then cast onto a 22-inch-wide stainless steel conveyer belt using a casting knife set at 2-5 mm gap opening. The cast material or film was subsequently dried into a flat sheet by conveying the film through a 200 feet convection tunnel dryer, comprising multiple heated zones (e.g., ranging from 80-150° C.). The sheet was dried to about 8 to 10% moisture. The flat sheet was separated from the belt, wound on a bobbin, and vacuum sealed in polyethylene bags to prevent moisture pickup and blocking during shipment. The bobbins were subsequently unwound and the sheet cut into strips (e.g., about 25-20 cuts per square inch).

TABLE 1

Cast sheet formulation- low MCC plus wood pulp

| Component | Percent by weight, dry weight basis |
|---|---|
| microcrystalline cellulose | 29-43 |
| wood pulp (4% solution) | 5-9 |
| carboxymethyl cellulose | 5-9 |
| glycerol | 40-60 |

Example 2. Cast Sheet Substrate Comprising Microcrystalline Cellulose

In another embodiment, a cast sheet substrate comprising the ingredients set forth in Table 2 below was prepared using the procedure of Example 1, but using a larger weight percent range of microcrystalline cellulose. The actual ingredients and percentages can be varied depending on the desired properties of the final product.

TABLE 2

Cast sheet formulation- high MCC plus wood pulp

| Component | Percent by weight, dry weight basis |
|---|---|
| microcrystalline cellulose | 38-56 |
| wood pulp (4% solution) | 7-11 |
| carboxymethyl cellulose | 7-11 |
| glycerol | 28-42 |

Example 3. Cast Sheet Substrate Comprising Microcrystalline Cellulose-Alginate Binder In one embodiment, a cast sheet substrate comprising the ingredients set forth in Table 3 below was prepared using the procedure of Example 1, but substituting sodium alginate for the carboxymethylcellulose. The actual ingredients and percentages can be varied depending on the desired properties of the final product.

TABLE 3

Cast sheet embodiment formulation- MCC plus wood pulp, alginate binder.

| Component | Percent by weight, dry weight basis |
|---|---|
| microcrystalline cellulose | 29-43 |
| wood pulp (4% solution) | 5-9 |
| sodium alginate | 5-9 |
| glycerin | 40-60 |

Results

The measured density and fill capacity for formulations prepared according to Examples 1-3 is provided in Table 4. Generally, sheet density decreased with alginate binder, while cut (22 cuts per inch) filler capacity increased.

TABLE 4

| Analytical results for formulations with MCC | | | | | | |
|---|---|---|---|---|---|---|
| | | | Basis weight | | | |
| | | Wt of square | (grams per square | Thickness | Density | Cut Filler Capacity |
| Sample description | | (g) | meter; gsm) | (cm) | (g/cm$^3$) | (cm$^3$/100 g) |
| Example 1 | mcc, CMC, 50% Glycerol | 6.337 | 281.6 | 0.0258 | 1.091 | 242 |
| Example 2 | mcc, CMC, 35% Glycerol | 4.138 | 183.9 | 0.0181 | 1.018 | 295 |
| Example 3 | mcc, Na alginate, 14% Glycerol | 3.392 | 146.3 | 0.0230 | 0.649 | 401 |

What is claimed is:

1. A substrate for use in an aerosol delivery device, the substrate comprising:

from about 30 to about 50% by weight of microcrystalline cellulose;

from about 5 to about 10% by weight of wood pulp;

from about 5 to about 10% by weight of carboxymethylcellulose or an alginate; and from about 30 to about 60% by weight of an aerosol forming material.

2. The substrate of claim 1, wherein the binder is carboxymethylcellulose.

3. The substrate of claim 1, wherein the binder is an alginate.

4. The substrate of claim 1, wherein the aerosol forming material is selected from the group consisting of water, polyhydric alcohols, polysorbates, sorbitan esters, fatty acids, fatty acid esters, non-fatty acid esters, waxes, cannabinoids, terpenes, sugar alcohols, and combinations thereof.

5. The substrate of claim 1, wherein the aerosol forming material is a polyhydric alcohol selected from the group consisting of glycerol, propylene glycol, 1,3-propanediol, diethylene glycol, triethylene glycol, and combinations thereof.

6. The substrate of claim 1, further comprising a flavorant, an active ingredient, or a combination thereof.

7. The substrate of claim 6, wherein the active ingredient comprises a nicotine component.

8. The substrate of claim 1, wherein the aerosol forming material is glycerol.

9. The substrate of claim 1, in the form of a sheet.

10. The substrate of claim 1, which is substantially free of tobacco material.

11. The substrate of claim 1, which is substantially free of nicotine.

12. An aerosol generating component for use with an aerosol delivery device, the aerosol generating component comprising the substrate of claim 1.

13. The aerosol generating component of claim 12, further comprising an aerosol-generating material, wherein the aerosol-generating material comprises a tobacco material.

14. The aerosol generating component of claim 13, further comprising a support, wherein the substrate is attached to the support.

15. The aerosol generating component of claim 14, wherein the support is planar.

16. The aerosol generating component of claim 12, wherein the substrate is blended with a tobacco material.

17. The aerosol generating component of claim 16, wherein the tobacco material is present as a plurality of strips.

18. The aerosol generating component of claim 12, comprising a plurality of strips of the substrate.

19. The aerosol generating component of claim 12, comprising multiple layers of the substrate.

20. An aerosol delivery device, comprising:

the aerosol generating component of claim 19;

a heat source configured to heat the aerosol generating component to form an aerosol; and an aerosol pathway extending from the aerosol generating component and extending along a length configured to convey the aerosol to a mouth portion of the aerosol delivery device.

21. The aerosol delivery device of claim 20, wherein the heat source comprises either an electrically powered heating element or a combustible ignition source.

22. The aerosol delivery device of claim 20, wherein the heat source is a combustible ignition source comprising a carbon-based material.

23. The aerosol delivery device of claim 20, wherein the heat source is an electrically-powered heating element.

24. The aerosol delivery device of claim 23, further comprising a power source electronically connected to the heating element.

25. The aerosol delivery device of claim 24, further comprising a controller configured to control power transmitted to the heating element by the power source.

26. The aerosol delivery device of claim 20, wherein the heat source is a conductive heat source or an inductive heat source.

* * * * *